US011123705B1

(12) United States Patent
Pannala et al.

(10) Patent No.: US 11,123,705 B1
(45) Date of Patent: Sep. 21, 2021

(54) METHOD AND REACTOR FOR CONVERSION OF HYDROCARBONS

(71) Applicant: SABIC Global Technologies B.V., Bergen op Zoom (NL)

(72) Inventors: Sreekanth Pannala, Sugar Land, TX (US); Byeongjin Baek, Katy, TX (US); Lei Chen, Sugar Land, TX (US); Vladimir Shtern, Houston, TX (US); Istvan Lengyel, Sugar Land, TX (US); David West, Bellaire, TX (US); Krishnan Sankaranarayanan, Missouri City, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 17/288,179

(22) PCT Filed: Oct. 23, 2019

(86) PCT No.: PCT/US2019/057603
§ 371 (c)(1),
(2) Date: Apr. 23, 2021

(87) PCT Pub. No.: WO2020/086681
PCT Pub. Date: Apr. 30, 2020

Related U.S. Application Data

(60) Provisional application No. 62/749,424, filed on Oct. 23, 2018.

(51) Int. Cl.
*B01J 19/00* (2006.01)
*B01J 19/24* (2006.01)
(Continued)

(52) U.S. Cl.
CPC ............ *B01J 19/246* (2013.01); *C07C 5/48* (2013.01); *C10G 9/36* (2013.01); *B01J 2219/0077* (2013.01); *B01J 2219/00094* (2013.01)

(58) Field of Classification Search
CPC .... B01J 19/2405; B01J 19/246; B01J 12/005; B01J 19/006; B01J 19/24; B01J 4/001;
(Continued)

(56) References Cited

U.S. PATENT DOCUMENTS 2,912,475 A 11/1959 Krause et al.
2,985,695 A 5/1961 Platz et al.
(Continued)

FOREIGN PATENT DOCUMENTS

CN 105586067 B 4/2018
GB 586027 A 3/1947
(Continued)

OTHER PUBLICATIONS

International Search Report and Written Opinion dated Jan. 17, 2020 in counterpart International PCT Application No. PCT/US2019/057603.

*Primary Examiner* — Sharon Pregler
(74) *Attorney, Agent, or Firm* — Grady K. Bergen; Griggs Bergen LLP; Paul I. Herman

(57) ABSTRACT

A reactor (12, 128, 198) and method for the conversion of hydrocarbon gases utilizes a reactor (12, 128, 198) having a unique feed assembly (58, 136, 200) with an original vortex disk-like inlet flow spaces (72, 74, 76, 80, 146, 148, 150, 152, 208, 216, 218), a converging-diverging vortex mixing chamber (116), and a cylindrical reactor chamber (40). This design creates a small combustion zone and an inwardly swirling fluid flow pattern of the feed gases that passes through a converging conduit (48) with a constricted neck
(Continued)

portion (54). This provides conditions suitable for efficient cracking of hydrocarbons, such as ethane, to form olefins.

20 Claims, 21 Drawing Sheets

(51) Int. Cl.
*C07C 5/48* (2006.01)
*C10G 9/36* (2006.01)

(58) Field of Classification Search
CPC .... B01J 19/0053; B01J 19/02; B01J 19/2415; B01J 19/26; B01J 6/008; C10G 9/36; C10G 2400/20; C07C 2/78; C07C 11/24; C07C 11/04; C07C 5/48; C07C 2/82; C07C 5/09; C07C 5/52; C07C 11/02
See application file for complete search history.

(56) References Cited

U.S. PATENT DOCUMENTS

| | | | |
|---|---|---|---|
| 3,000,989 A | 9/1961 | Larcher et al. | |
| 3,704,332 A | 11/1972 | Lindstrom | |
| 3,842,138 A | 10/1974 | Chahvekilian et al. | |
| 3,959,401 A | 5/1976 | Albright et al. | |
| 4,256,565 A | 3/1981 | Friedman et al. | |
| 4,613,426 A | 9/1986 | Okamoto et al. | |
| 5,886,056 A | 3/1999 | Hershkowitz et al. | |
| 6,365,792 B1 | 4/2002 | Stapf et al. | |
| 7,074,977 B2 | 7/2006 | Rapier et al. | |
| 7,819,656 B2 | 10/2010 | Ponzi et al. | |
| 7,956,228 B2 | 6/2011 | Bartenbach et al. | |
| 8,801,814 B2 | 8/2014 | Grossschmidt et al. | |
| 2002/0064741 A1 | 5/2002 | Bartenbach et al. | |
| 2011/0054231 A1 | 3/2011 | Peterson | |
| 2014/0058158 A1 | 2/2014 | Bedard et al. | |
| 2015/0165414 A1* | 6/2015 | Gattupalli | C07C 2/78 585/536 |

FOREIGN PATENT DOCUMENTS

| | | |
|---|---|---|
| GB | 821856 A | 10/1959 |
| GB | 834419 A | 5/1960 |
| GB | 839200 A | 6/1960 |
| GB | 865732 A | 4/1961 |
| GB | 889258 A | 2/1962 |
| WO | WO2014027985 A1 | 2/2014 |
| WO | WO2015028539 A1 | 3/2015 |
| WO | WO2018044557 A1 | 3/2018 |

* cited by examiner

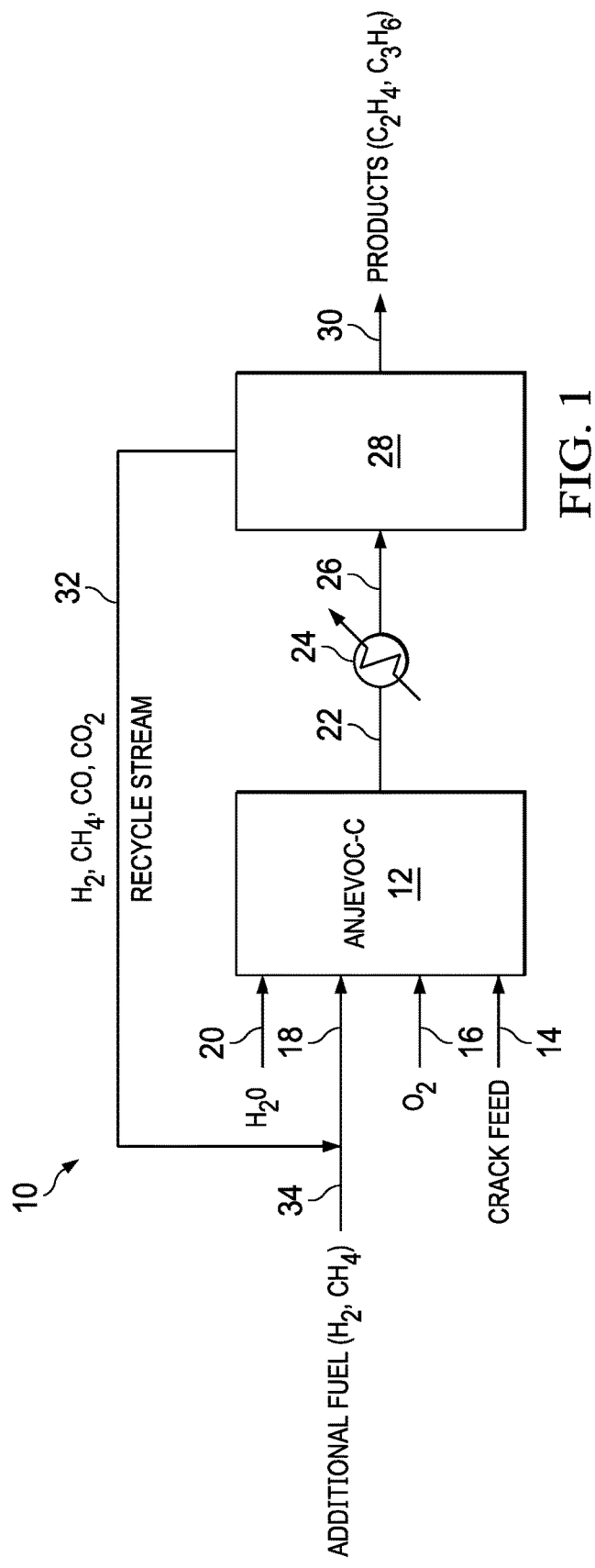
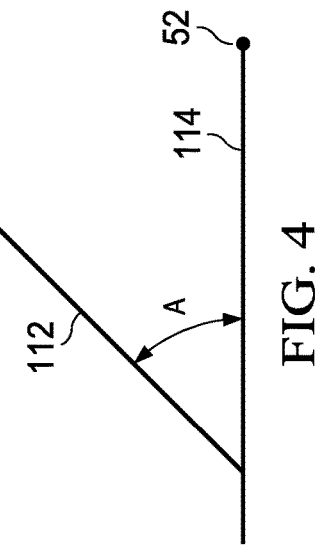

METHOD AND REACTOR FOR CONVERSION OF HYDROCARBONS

CROSS-REFERENCE TO RELATED APPLICATIONS

This application is a national stage application under 35 U.S.C. § 371 of International PCT Application No. PCT/US2019/057603, filed Oct. 23, 2019, which claims the benefit of U.S. Provisional Application No. 62/749,424, filed Oct. 23, 2018, each of which is incorporated herein by reference in its entirety.

TECHNICAL FIELD

The invention relates to conversion methods for converting a variety of hydrocarbons to produce more valuable products and the reactor designs for such conversion.

BACKGROUND

A single-stage combustion pyrolysis method to produce acetylene was developed by BASF, which is described in U.S. Pat. No. 5,789,644. This process has been commercialized at a 50 KTA scale using multiple reactors in Germany and the U.S. In this process, natural gas serves for the hydrocarbon feed and pure oxygen serves as the oxidant to generate heat, which is critical for acetylene production. The two streams are premixed in a diffuser, and the premixed fuel rich gas is burnt using a burner block through partial oxidation. A major disadvantage of such a design is the flashback risks of the premixed flame under various feedstock and operating conditions, as well as the plurality of burners used, which increases the total cost of operation, difficulties in heat control, and low carbon yield toward olefin product. Furthermore, while acetylene used to be the building block for chemicals, over the last six to seven decades olefins have become the building blocks of the chemical industries and there is a desire to directly produce olefins rather than the indirect hydrogenation route using acetylene.

Conventional steam crackers are the industry go-to reactors to break long-chain hydrocarbons and modify smaller alkanes (i.e., naphtha, butane, ethane) into smaller molecules and olefins, such as ethylene and propylene. In such crackers, heavy gases such as naphtha, liquefied petroleum gas (LPG), propane, butane, and ethane are fed into a furnace with steam and converted into smaller olefins. Steam is added to the process to increase the selectivity to olefins with reasonable conversion. Typically, this process operates at high temperatures (i.e., from 750° C. to 900° C.) and has residence times of around 100 to 500 milliseconds. This process has been optimized over the last five decades but there are still significant disadvantages. These include heat losses and complexity associated with separate exothermic (combustion in the furnace) and endothermic steps (cracking in the process tubes). The presence of inert compounds in the combustion and process side also affects the overall efficiency. Metallurgical limitations of the reactors also limit the temperatures that can be used. Ideally, higher temperatures with shorter contact times result in better selectivity and conversion to smaller olefins. Plugging from coking also occurs in these conventional processes, which can increase the capital cost and operational expenses. This also prevents cracking certain heavier feeds. There is also a lack of feedstock flexibility, as commercial crackers are typically optimized for only a certain type of feedstock. Typically, these crackers also operate at process pressures less than 200 kPa and that increases the capital cost of the downstream operations.

The proposed invention addresses many of the shortcomings of these conventional reactors.

SUMMARY

A reactor system for the conversion of hydrocarbons comprises a reactor vessel having a reactor wall that defines a reaction chamber. The reactor system includes a reactor inlet assembly that has a converging conduit with a circumferential wall that surrounds a central longitudinal axis and extends from opposite upstream and downstream ends of the converging conduit. The circumferential wall tapers in width from the downstream and upstream ends to an annular constricted neck portion located between the downstream and upstream ends of the converging conduit. The downstream end of the converging conduit is in fluid communication with the reaction chamber of the reactor. The upstream end of the converging conduit forms an inlet of the reactor inlet assembly.

A feed assembly of the reactor system is in fluid communication with the inlet of the reactor inlet assembly, with the central axis passing through the feed assembly. The feed assembly comprises a downstream feed assembly wall extending circumferentially around and joining the upstream end of the reactor inlet assembly, the downstream feed assembly wall being oriented perpendicular or substantially perpendicular to the central axis. An upstream feed assembly wall is axially spaced upstream from the downstream feed assembly wall along the central axis and extends perpendicularly or substantially perpendicularly across the central axis. An upstream gas partition wall and a downstream gas partition wall are each axially spaced between the downstream and upstream feed assembly walls and are axially spaced from one another. The upstream gas partition wall and the downstream gas partition wall or circumferential portions thereof are oriented perpendicular or substantially perpendicular to the central axis. At least one of the upstream gas partition wall and downstream gas partition wall terminates at a position upstream from the converging conduit to define a central opening that surrounds the central axis of the converging conduit. An upstream annular inlet flow space is defined between the upstream feed assembly wall and the upstream partition wall. A downstream annular inlet flow space is defined between the downstream feed assembly wall and the downstream gas partition wall.

The annular inlet flow spaces cause introduced feeds to flow perpendicularly to the central axis of the converging conduit in an inwardly swirling fluid flow pattern within said flow spaces about the central axis of the converging conduit.

The area extending from the central opening of the at least one of the upstream and downstream partition walls to the inlet of the reactor inlet assembly defines a central chamber of the feed assembly, with heated combustion gases from at least one of the inlet flow spaces being discharged into the central chamber. The hydrocarbon feed and heated combustion gases passing as swirling gases through the converging conduit to the reaction chamber.

In particular embodiments, at least one of the annular inlet flow spaces is provided with circumferentially spaced apart guide vanes oriented to facilitate the swirling fluid flow within said at least one of the inlet flow spaces. The guide vanes may be movable to selected positions and tilting angles to provide selected azimuthal-to-radial velocity ratios of fluids flowing within the annular inlet flow spaces. In some embodiments, the guide vanes are configured as non-planar airfoils.

In certain instances, the reactor wall is cylindrical. The circumferential wall of the converging conduit from the downstream end to the annular constricted neck portion, and optionally an upstream portion of the reactor wall of the reaction chamber that joins the circumferential wall of the converging conduit, may be configured as a smooth, continuous wall that follows contour lines of an ellipsoidal cap or spherical cap shape. The interior of the reactor wall may be a refractory material.

In some embodiments, the downstream gas partition wall has an extended portion that is spaced from and follows the contours of the circumferential wall of the converging conduit of the reactor inlet assembly and terminates at a position downstream of the annular constricted neck portion so that a downstream inlet flow space is defined that discharges into an area downstream from the constricted neck portion.

In some applications, the intermediate annular gas inlet flow space is divided by an intermediate gas partition wall having a central opening that surrounds the central axis of the converging conduit and divides the intermediate inlet flow space into upstream and downstream intermediate annular inlet flow spaces that constitute inlet flow spaces for introducing a fuel gas feed and an oxidizer feed. In others, the upstream annular gas inlet flow space and the intermediate inlet flow space constitute inlet flow spaces for introducing a fuel gas feed and an oxidizer feed.

In certain embodiments, a cooling gas feed assembly is in fluid communication with at least one of the reaction chamber and the reactor inlet assembly. The cooling gas feed assembly includes a pair of axially spaced apart cooling gas feed assembly walls oriented perpendicular or substantially perpendicular to the central axis. An annular cooling gas inlet flow space is defined between the cooling gas feed assembly walls and communicates with said at least one of the reaction chamber and the reactor inlet assembly. The annular cooling gas inlet flow space may be provided with circumferentially spaced apart guide vanes oriented to facilitate the swirling fluid flow within the cooling gas inlet flow space.

In a method of cracking hydrocarbons to cracked hydrocarbon products, a hydrocarbon feed containing hydrocarbons to be cracked is introduced into a reactor system. The reactor system comprises a reactor vessel having a reactor wall that defines a reaction chamber. A reactor inlet assembly has a converging conduit with a circumferential wall that surrounds a central longitudinal axis and extends from opposite upstream and downstream ends of the converging conduit. The circumferential wall tapers in width from the downstream and upstream ends to an annular constricted neck portion located between the downstream and upstream ends of the converging conduit. The downstream end of the converging conduit is in fluid communication with the reaction chamber of the reactor. The upstream end of the converging conduit forms an inlet of the reactor inlet assembly.

The reactor system used in the method further includes a feed assembly in fluid communication with the inlet of the reactor inlet assembly, with the central axis passing through the feed assembly. The feed assembly includes a downstream feed assembly wall that extends circumferentially around and joins the upstream end of the reactor inlet assembly. The downstream feed assembly wall is oriented perpendicular or substantial perpendicular to the central axis. The feed assembly also includes an upstream feed assembly wall that is axially spaced upstream from the downstream feed assembly wall along the central axis and extends perpendicularly or substantially perpendicularly across the central axis. An upstream gas partition wall and a downstream gas partition wall are each axially spaced between the downstream and upstream feed assembly walls and are axially spaced from one another. The upstream gas partition wall and the downstream gas partition wall or circumferential portions thereof are oriented perpendicular or substantially perpendicular to the central axis. At least one of the upstream gas partition wall and downstream gas partition wall terminates at a position upstream from the converging conduit to define a central opening that surrounds the central axis of the converging conduit. An upstream annular inlet flow space is defined between the upstream feed assembly wall and the upstream partition wall. A downstream annular inlet flow space is defined between the downstream feed assembly wall and the downstream gas partition wall. An intermediate inlet flow space is defined between the upstream gas partition wall and the downstream gas partition wall.

The annular inlet flow spaces cause introduced feeds to flow perpendicularly or substantially perpendicularly toward the central axis of the converging conduit in an inwardly swirling fluid flow pattern within said flow spaces about the central axis of the converging conduit. The area extending from the central opening of the at least one upstream and downstream partition walls to the inlet of the reactor inlet assembly defines a central chamber of the feed assembly.

In the method, a cracking feed of the hydrocarbon feed to be cracked is introduced into a first inlet flow space and a fuel gas feed and an oxidizer feed are introduced into adjacent second and third inlet flow spaces so that the feeds pass through said flow spaces perpendicularly or substantially perpendicularly toward the central axis of the converging conduit in an inwardly swirling fluid flow pattern within said flow spaces flowing about the central axis of the converging conduit. The order of fuel feed and oxidizer feed may be altered in some applications. The fuel gas feed and oxidizer feed combust in the central chamber to form heated combustion gases. The hot combustion gases and cracking feed are discharged into the central chamber and/or reaction chamber so that the heated combustion gases and cracking feed are mixed together and form a swirling, heated gas mixture.

The heated gas mixture is allowed to react within the reaction chamber of the reactor vessel under reaction conditions suitable for hydrocarbon cracking, with at least a portion of the cracking feed of the gas mixture being converted to cracked hydrocarbon products. Cracked hydrocarbon product is removed from the reaction chamber of the reactor vessel.

In particular embodiments, the fuel gas feed, which may comprise a hydrogen-containing gas of at least one of hydrogen gas ($H_2$) and methane ($CH_4$), is introduced into one of the first and second annular fuel gas inlet flow spaces. An oxidizer feed, which comprises an oxygen-containing gas, is introduced into the other of the first and second annular fuel gas inlet flow spaces.

The hydrogen-containing gas may be introduced into the feed assembly to provide an excess of hydrogen that is from 1 to 5 times that required for cracking the hydrocarbon feed The cracking feed may include at least one of ethane, liquefied petroleum gas, butane, naphtha, natural gas, light gas oils, and heavy gas oils, the cracking feed optionally being premixed with steam.

At least one of hydrogen gas (H$_2$), methane, and carbon oxides or combinations thereof may be separated from the removed cracked hydrocarbon product and recycled to the feed assembly.

The azimuthal-to-radial velocity ratio of each of the feeds and the oxygen gas feed stream within the annular flow spaces may be from 0 to ∞, more particularly from 0 to 30.

Each of the feeds may each be introduced into the respective annular flow spaces in the same rotational direction. In certain applications, at least one of the annular inlet flow spaces is provided with circumferentially spaced apart guide vanes oriented to facilitate the spiraling fluid flow within said at least one of the inlet flow spaces. The guide vanes may be movable to selected positions and tilting angles to provided selected azimuthal-to-radial velocity ratios of the fluid flow within said at least one of the inlet flow spaces.

In some embodiments, the reactor wall is cylindrical. The circumferential wall of the converging conduit from the downstream end to the annular constricted neck portion, and optionally an upstream portion of the reactor wall of the reaction chamber that joins the circumferential wall of the converging conduit, may be configured as a smooth, continuous wall that follows contour lines of an ellipsoidal cap or spherical cap shape. The interior of the reactor wall may be a refractory material.

The residence time of the gas mixture within the reactor system is 50 milliseconds or less in certain instances. The reaction conditions may include a temperature of from 900° C. to 1300° C. and a pressure of from 0 kPa (g) to 10,000 kPa (g) at an outlet of the reactor.

In certain embodiments of the method, the reactor system further comprises a cooling gas feed assembly in fluid communication with at least one of the reaction chamber and the reactor inlet assembly. The cooling gas feed assembly comprises a pair of axially spaced apart cooling gas feed assembly walls oriented perpendicular or substantially perpendicular to the central axis. An annular cooling gas inlet flow space is defined between the cooling gas feed assembly walls that communicates with said at least one of the reaction chamber and the reactor inlet assembly where cooling gases from the cooling gas feed assembly are introduced.

BRIEF DESCRIPTION OF THE DRAWINGS

For a more complete understanding of the embodiments described herein, and the advantages thereof, reference is now made to the following descriptions taken in conjunction with the accompanying figures, in which:

FIG. 1 is a process flow diagram of a cracking system for cracking of hydrocarbons into cracked hydrocarbon products in accordance with particular embodiments of the invention;

FIG. 4 is schematic showing the angle of guide vanes of the reactor feed assembly of the reactor of FIG. 2 relative to a central longitudinal axis of the reactor;

DETAILED DESCRIPTION

Figure 2:
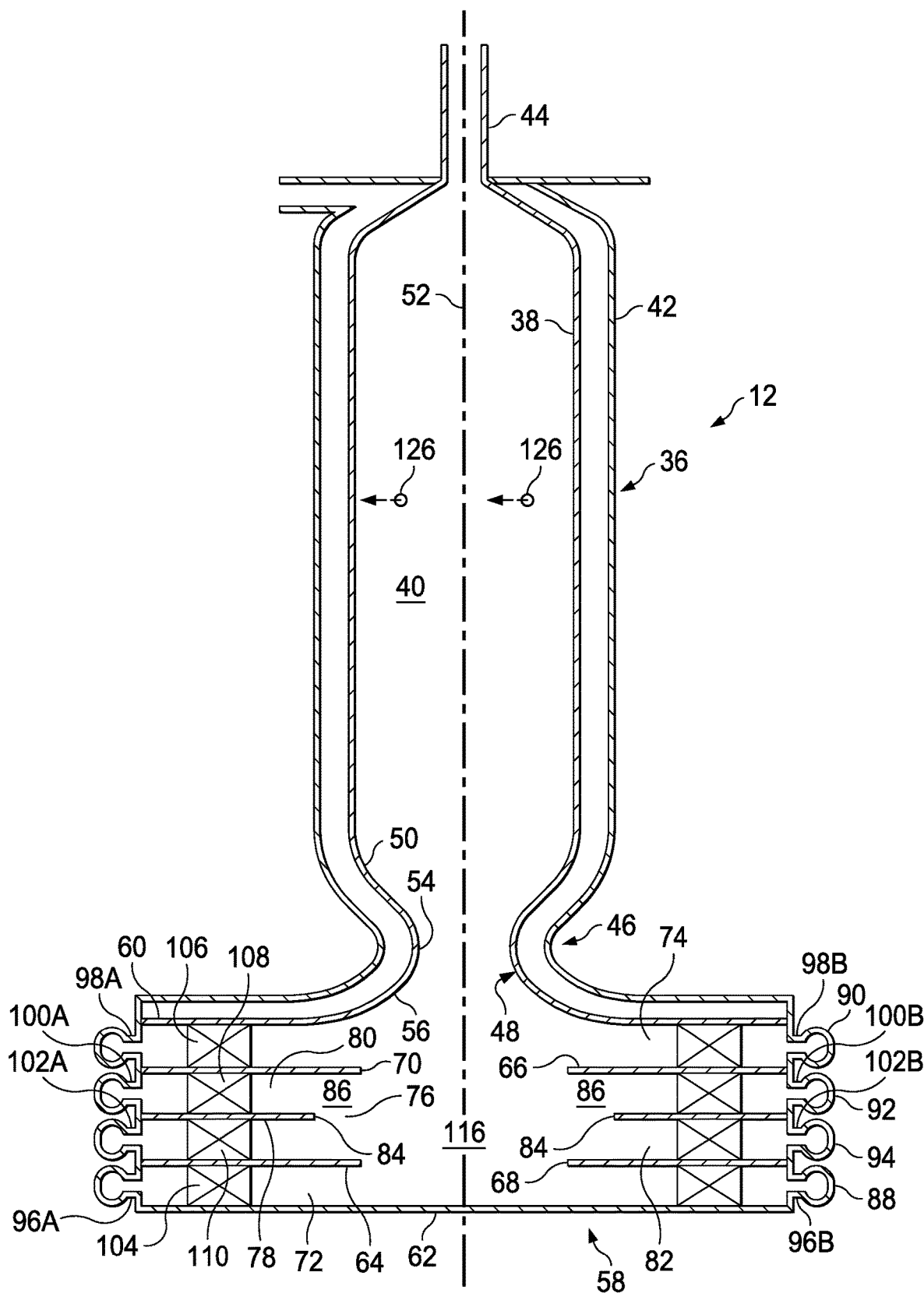
FIG. 2 is a schematic representation of a reactor system for cracking shown in cross section and constructed in accordance with particular embodiments of the invention.

In the present disclosure, a novel system is utilized that converts hydrocarbons to higher value products, such as olefins, by utilizing high centrifugal forces generated by swirling flow in a unique reactor configuration to create and control a reacting flow environment that maximizes the production of desirable olefins with very high productivity (cracking). This is achieved by utilizing annular highly swirled jets of feed gases where hydrogen (or other fuels such as natural gas, recycled syngas, etc.) and oxygen gases are mainly used to generate the heat required for cracking of hydrocarbons. The cracking reactor used is similar to the pyrolysis reactor described in U.S. Patent Application No. 62/639,577 and International Publication No. WO2019/173570A1, each of which is incorporated by reference herein for all purposes. U.S. Patent Application No. 62/639,577 and International Publication No. WO2019/173570A1 each describe a reactor that can be used in the pyrolysis conversion of hydrocarbon gases. This type of reactor may be referred to as an ANJEVOC (ANnular JEt VOrtex Chamber) reactor. The ANJEVOC reactor described herein, while similar to that described in U.S. Patent Application No. 62/639,577 and International Publication No. WO2019/173570A1, is used for cracking and therefore is configured differently. Such reactor may be referred to as the ANJEVOC-C (ANnular JEt VOrtex Chamber—Cracking) reactor.

Referring to FIG. 1, a flow schematic of a hydrocarbon conversion system 10 is shown for the conversion of hydrocarbons to higher value products, such as olefins. The system 10 includes an ANJEVOC-C cracking reactor 12, which is described in more detail later on. A cracking feed 14 is fed to the reactor 12 as a separate stream. The cracking feed 14 can include hydrocarbons such as ethane, liquefied petroleum gas (LPG), butane, naphtha, natural gas, light gas oils, and/or heavy gas oils. The cracking feed stream 14 may be preheated prior to being introduced into the reactor 12. In particular applications, the feed stream 14 may be heated to a temperature of from 25° C. to 500° C. to improve conversion efficiency or vaporize heavier liquid hydrocarbons either externally or within the reactor It should be noted in the description, if a numerical value, concentration or range is presented, each numerical value should be read once as modified by the term "about" (unless already expressly so modified), and then read again as not so modified unless otherwise indicated in context. Also, in the description, it should be understood that an amount range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific points within the range, or even no point within the range, are explicitly identified or referred to, it is to be understood that the inventor appreciates and understands that any and all points within the range are to be considered to have been specified, and that inventor possesses the entire range and all points within the range.

An oxygen-containing gas feed 16 for combustion of a hydrogen-rich fuel gas feed 18 is also fed to the reactor 12 as a separate stream. The oxygen-gas feed 16 may be a concentrated oxygen-gas feed, wherein a majority of the feed (i.e., >50 mol %) is composed of oxygen gas ($O_2$). In many instances, the oxygen-containing gas will be a high-purity oxygen-containing gas feed composed of $O_2$ in an amount of from 20 mol % to 100 mol % of the oxygen gas feed stream. This may be that provided from an air separation unit (not shown) used for separating oxygen gas from air or other oxygen-gas source. Air may also be used as the oxygen-containing gas. In cases where air is used as the oxygen-containing gas, or cases where there are large amounts of impurities (e.g., $N_2$) in the oxygen-containing gas feed, separation of such impurities from the product may be necessary downstream.

A steam or water ($H_2O$) feed is also feed to the reactor 12 as separate steam feed stream 20. The cracking feed 14, fuel 18, and/or oxygen-gas feed 16 may also be premixed with steam in certain embodiments. In some instances, the separate steam feed stream 20 may be eliminated where sufficient steam is provided and mixed with the feeds 14 and/or 16.

Cracked reaction products 22 are removed from the reactor 12 where they may be cooled by quenching in a quenching unit 24, such as a water-droplet-spray quench vessel, or other suitable gas quench devices. The cracked products 22 will typically be a mixture of hydrogen gas, steam, oxygenates, some heavies (>C4), some aromatics, and product olefins.

The quenched cracked reaction products 26 may be delivered to a separation unit 28, where the product gases are separated to form a product stream 30 containing product olefins, such as ethylene ($C_2H_4$), propylene ($C_3H_6$), and others, and a separated gas stream 32.

The separated gas stream 32 is removed from the separator 28 and will typically contain hydrogen gas ($H_2$), with minor amounts of methane ($CH_4$), and carbon oxides of CO and $CO_2$. In certain applications, $CO_2$ can be separated before separating other gases so that recycled gas stream 32 may contain only $H_2$, $CH_4$, and CO. Because dehydrogenation occurs during the cracking reaction, enough hydrogen is typically generated so that it can be used as a fuel gas for generating heat for the cracking reaction in reactor 12. Thus, the gas stream 32 may be recycled and fed as the hydrogen-rich fuel feed 18. In some cases, enough fuel gas (e.g., $H_2$) is recycled during the cracking reaction so that no additional fuel is needed in addition to that supplied by the recycle stream 32. In other cases, however, additional fuel feed 34 of a hydrogen-rich or natural gas feed may be used for the fuel feed 18, such as an initial fuel feed during reactor startup, or that is combined with the recycle stream 32 to form the fuel feed 18 when an insufficient amount of hydrogen is available in the recycle stream 32 for combustion reaction heat.

Based upon the type of cracking feed, the operational conditions of the reactor 12 may vary. In a typical cracking reaction using the ANJEVOC-C reactor, the oxygen feed 16 is typically used with excess hydrogen or fuel gas so that all the oxygen is consumed. Usually, the amount of hydrogen will be 1 or 2 to 4 times the stoichiometric amount needed for combustion with oxygen. In some cases, hydrogen is sub-stoichiometric (below 1) to allow for additional exothermic reactions in the mixing zone. The oxygen feed 16 may provide an oxygen equivalent-to-fuel mole ratio of from 0.125 to 0.50. Furthermore, the ratio between the crack feed to hydrogen fuel will typically range from 1.0 to 15 based on mass depending on the hydrocarbon feed. The residence time within the reactor 12 may range from 50 milliseconds or less, more particularly from 20 milliseconds or less. As will be discussed in more detail later on, recirculation zone temperature within the reactor will typically range from 1000° C. to 1300° C. The pressure at the reactor outlet may vary. A suitable pressure at the reactor outlet may range from 0 kPa (g) to 10,000 kPa (g), more particularly from 0 kPa (g) to 1,000 kPa (g).

It should be noted that while the system 10 of FIG. 1 shows single units for the various process steps, each unit could be composed of one or more units that may operate in conjunction with one another, such as parallel or sequentially, to carry out the various process steps described.

Referring to FIG. 2, an elevational cross-sectional schematic representation of the cracking reactor system 12 for cracking of hydrocarbons, such as ethane, LPG, butane, naphtha, natural gas, light gas oils, heavy gas oils, or a combination of these hydrocarbons, is shown. The reactor 12 constitutes an ANJEVOC-C reactor and includes a reactor vessel 36 having a reactor wall 38 that defines an interior reaction chamber 40. The reactor wall 38 may have a cylindrical configuration with a constant diameter along all or a portion of its length, which may constitute a majority of its length. In most instances, the reactor 12 is oriented vertically so that the cylindrical reactor wall 38 is oriented in an upright orientation. The reactor can have other orientations (e.g., horizontal, sloped, or downward), however, because the process is controlled by the centrifugal force, which exceeds the gravitational force by several orders of magnitude. The reactor vessel 36 may be configured to provide a length to diameter ratio (L/D) of at least 2. In particular applications, the L/D ratio may range from 2-10, more particularly from 2-5.

The reactor vessel 36 may be formed from steel. In certain embodiments, a cooling jacket can be provided around the reactor vessel, wherein a second steel wall 42 is positioned around and spaced from the inner reactor wall 38 and a cooling fluid, such as water may be circulated through the jacket formed between the walls 38, 42. In other embodiments, the reactor wall 38 may be formed from one or more layers of refractory material that line the interior of an outer steel wall to reduce heat loss and sustain the high temperatures of the reactor 12. As will be described later on, because of the unique design and operation of the reactor 12, the reactor wall 38 is cooled internally by the high-velocity near-wall gas flow pushed by centrifugal forces against the reactor wall 38 so that in some applications no exterior cooling jacket is required. This also allows refractory materials to be used for the interior of the reactor wall 38. Refractory materials (without cooling) typically cannot be used with conventional cracking reactors with pure oxygen due to the higher temperatures (e.g., from 2000° C. to 2800° C.) encountered.

An outlet 44 is provided at the upper or downstream end of the reactor vessel 36 for removing or discharging cracked products from the reaction chamber 40. Although the outlet 44 is shown located at the upper end of the reactor vessel 36, in other embodiments it may be located at the lower end of the reactor vessel 36, so that the flow through the reactor is in the opposite direction (i.e., from top to bottom). The outlet diameter can be same as the diameter of the reactor wall 38 or the outlet diameter may be reduced to accelerate the flow before quenching and collection downstream.

The reactor 12 includes a reactor inlet assembly 46 that is coupled or joined to the lower or upstream end of the reactor wall 38 of the reactor vessel 36. The inlet assembly 46 has a converging conduit 48 with a circumferential wall 50 that surrounds a central longitudinal axis 52 of the reactor. Where the reactor 12 is oriented vertically, the central axis 52 will also be oriented vertically as well and will be concentric with or parallel to a central vertical axis of the reactor vessel 36. In the embodiment shown, the axis 52 is concentric with and aligned with the central longitudinal axis of the reactor vessel 36. The circumferential wall 50 extends from opposite upstream and downstream ends of the converging conduit 48. As used herein, the terms "upstream" and "downstream" or similar expressions with respect to describing various components of the reactor system 12 shall refer to the position of the component with respect to the direction of overall fluid flow through the reactor 12 along the central axis 52. As can be seen in FIG. 2, the circumferential wall 50 smoothly tapers in width or diameter from the downstream and upstream ends to an annular constricted neck portion 54 located between the downstream and upstream ends of the converging conduit 48. The interior of the circumferential wall 50 may have a circular perpendicular transverse cross section (with respect to the axis 52) along its length. The circumferential wall 50 defines an interior flow path of the inlet assembly 46 with the constricted neck portion 54 forming a converging-diverging streamlined nozzle of the inlet assembly 46. The nozzle geometry of the neck portion 54 is configured based upon the theory relating to swirling conical jets of a viscous incompressible fluid.

The circumferential wall 50 of the converging conduit 48 from the downstream end where it joins reactor wall 38 to the annular constricted neck portion 54 may, in some embodiments, be configured as a smooth, continuous concave wall having an ellipsoidal cap or spherical cap shape or configuration. Likewise, the upstream portion of the reactor wall 38 of the reaction chamber 40 that joins the circumferential wall 50 of the converging conduit 48 may also be configured as a smooth, continuous concave wall that follow contour lines of an ellipsoidal cap or spherical cap shape or configuration.

The downstream end of the converging conduit 48 joins the reactor wall 38 around its perimeter so that the converging conduit 48 is in fluid communication with the reactor chamber 40 of the cracking reactor vessel 36. The upstream end of the converging conduit 48 forms a reactor inlet 56 of the reactor vessel 36.

A reactor feed assembly 58 is provided with the reactor 12. The reactor feed assembly 58 is in fluid communication with the reactor inlet 56 of the inlet assembly 46, with the central axis 52 passing through the reactor feed assembly 58. The feed assembly 58 includes a downstream feed assembly wall 60 that extends circumferentially around and joins the upstream end of the reactor inlet 56. The feed assembly wall 60 or circumferential portions thereof are oriented perpendicularly or substantially perpendicularly (i.e., ≤5 degrees from perpendicular about its circumference as it extends radially from the central axis) to the central axis 52.

Axially spaced upstream from the downstream wall 60 along the central axis 52 is an upstream feed assembly wall 62. The upstream wall 62 or circumferential portions thereof are oriented perpendicular to or substantially perpendicularly (i.e., ≤5 degrees from perpendicular about its circumference as it extends radially from the central axis) to the central axis 52 and extends across the central axis 52.

An upstream gas partition wall 64 and a downstream gas partition wall 66 are axially spaced between the downstream and upstream feed assembly walls 60, 62 and are axially spaced from one another, with the upstream wall 64 being positioned upstream from the downstream partition wall 66. The partition walls 64, 66 or circumferential portions thereof are also each oriented perpendicularly to or substantially perpendicularly (i.e., ≤5 degrees from perpendicular about its circumference as it extends radially from the central axis) to the central axis 52. The inner ends of the partition walls 64, 66 terminate at a position below the converging conduit 48 to define a central opening 68, 70, respectively, that surrounds the central axis 52 and is concentric with the converging conduit 48. The central openings 68, 70 each have a circular configuration. Other shapes for the central openings 68, 70 (e.g., oval) may also be used provided such configuration facilitates the swirling of gases to provide the required flow patterns described herein. This shape may also correspond to the cross-sectional shape of the circumferential wall 50 of the converging conduit 48. In most applications, however, the central openings 68, 70 will be circular in shape. The central openings 68, 70 may have a diameter or width that is the same or slightly different than the diameter or width of the constricted neck 54 of the converging conduit 48 at its narrowest point.

The upstream partition wall 64 defines an annular gas flow space 72 located between the upstream feed assembly wall 62 and the upstream side of the upstream partition wall 64. In the embodiment shown, the flow space 72 constitutes an upstream annular hydrocarbon cracking feed inlet flow space. Likewise, an annular gas flow space 74 is defined by the downstream side of the downstream partition wall 66 and the downstream feed assembly wall 60. In the embodiment shown, the flow space 74 constitutes an annular steam or water inlet flow space.

A further annular flow space 76 is defined between the upstream side of the downstream gas partition wall 66 and the downstream side of the upstream gas partition wall 64. An intermediate partition wall 78 is axially spaced between the downstream gas partition wall 66 and the upstream gas partition wall 64 to define downstream and upstream intermediate annular gas inlet flow spaces 80, 82. The intermediate partition wall 78 or circumferential portions thereof is also oriented perpendicularly to or substantially perpendicularly (i.e., ≤5 degrees from perpendicular about its circumference as it extends radially from the central axis) to the central axis 52. In the embodiment shown, the intermediate partition wall constitutes a fuel gas partition wall that defines the flow spaces 80, 82, which constitute first and second annular fuel gas inlet flow spaces. The inner end of the intermediate partition wall 78 terminates to define a central opening 84 that surrounds the central axis 52 of the converging conduit 48, and wherein the periphery of the central opening 84 of the fuel gas partition wall 78 is spaced radially outward a distance from the central openings 68, 70 of the upstream gas partition wall 64 and the downstream gas partition wall 66, as is shown. The area spaced radially inward from the central opening 84 of the intermediate partition wall 78 between the upstream and downstream gas partition walls 64, 66 defines an annular combustion zone 86. The size of the central opening 84 can vary to fit the radial extent of combustion zone 86.

This configuration provides flow passages through which hydrocarbon gas feed to be cracked, steam, oxygen gas, and hydrogen-rich fuel for providing combustion heat can each be separately introduced and passed through the flow spaces 72, 74, 80, 82, respectively, perpendicularly or substantially perpendicular to the central axis 52 of the converging conduit 48. In some instances, the lowermost or upstream flow space 72 will constitute a hydrocarbon cracking feed inlet flow space. The steam feed may be introduced into the uppermost or upstream annular steam inlet flow space 74. In other instances, the hydrocarbon cracking feed may be introduced into the uppermost or downstream flow space 74 and the steam feed may be introduced into the lowermost or upstream flow space 72. A fuel gas feed comprised of an hydrogen-rich gas feed may be introduced into one of the first and second adjacent annular fuel gas inlet flow spaces 80, 82, with an oxidizer or oxygen-containing gas feed being introduced into the other of the flow spaces 80, 82. The downstream flow space 80 may be used for delivering the oxidizer or oxygen-containing gas and the upstream flow space 82 will be used for delivering the hydrogen-rich fuel gas. In other instances, these may be reversed or altered in other sequences.

The flow passages 72, 74, 80, 82 are configured so that the different feeds pass through flow spaces perpendicularly or substantially perpendicularly to the central axis 52 of the converging conduit 48 in an inwardly swirling fluid flow pattern within said flow spaces so that the feeds flow about the central axis 52 of the converging conduit 48. The fuel gas and oxidizer feeds combust primarily in the small combustion zone 86 between the upstream and downstream partition walls 64, 66 within the central opening 84 of the fuel gas partition wall 78.

The walls 60, 62, 64, 66, and 78 forming the different flow spaces 72, 74, 80, 82 may be parallel to one another in many cases, but may be non-parallel to one another in certain cases. The walls 60, 62, 64, 66, and 78 are axially spaced apart to provide the desired volume and flow characteristics for the gases flowing through them. This may be based upon the desired flow rates or linear velocities of each of the feed gases and their relative amounts. For instance, the relative volume of oxygen gas needed for the combustion is typically smaller than that of the hydrogen-rich fuel gas needed for the combustion. Therefore, the partition wall 78 may be spaced closer to the downstream partition wall 66 so that the flow space 82 for the hydrogen fuel is larger to accommodate the greater flow of fuel gas. The particular spacing may depend on fuel gas and oxidizer combination, the desired volume for combustion, and cracking feeds.

Annular gas manifolds 88, 90, 92, 94 may be provided around the outer periphery of the flow spaces 72, 74, 80, 82, respectively. The gas manifold 88 is fluidly coupled to a cracking feed source, such as cracking feed 14 of FIG. 1. The manifold 90 is fluidly coupled to a steam source, such as the steam feed 20 of FIG. 1. The manifold 92 is fluidly coupled to an oxygen-containing-gas source, such as the oxygen gas feed 16 of FIG. 1. And the manifold 92 is fluidly coupled to a hydrogen-rich or fuel feed source, such as the fuel feed 18 of FIG. 1. The manifolds 88, 90, 92, 94 are provided with the reactor feed assembly 58 to facilitate introduction of feed gases into the flow spaces 72, 74, 80, 82.

Gas inlets 96, 98, 100, 102 from the manifolds 88, 90, 92, 94, respectively, may be directed tangentially into the flow spaces 72, 74, 80, 82 so that the gases are not directed only radially toward the central axis 52 from the inlets 96, 98, 100, 102, but instead are directed mostly tangentially around the central axis 52 to provide an inwardly swirling flow pattern. As shown in FIG. 2, each flow space 72, 74, 80, 82 may have one or more tangential inlets, such as the inlets 96A and 96B, 98A and 98B, 100A and 100B, and 102A and 102B. Furthermore, the walls 60, 62, 64, 66, and 78 forming the different flow spaces of the feed assembly 58 keep the gases introduced from the manifolds 88, 90, 92, 94 from flowing axially along the central axis 52 while they are contained within the flow spaces 72, 74, 80, 82. The manifolds 88, 90, 92, 94 can be configured as standard manifolds (e.g., snail-like) as may be typically used in vortex devices.

Figure 3:
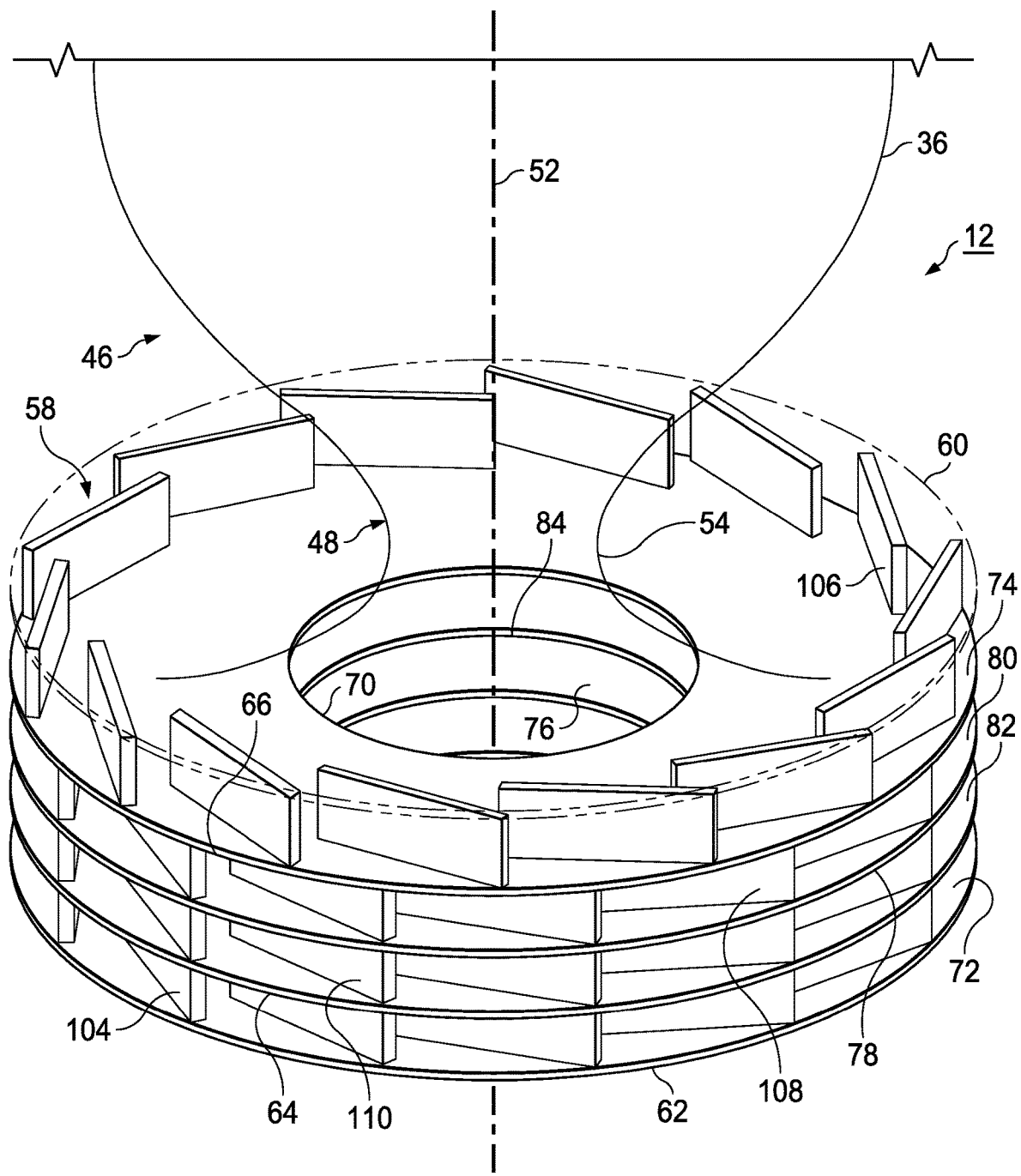
FIG. 3 is perspective view of a lower or upstream portion of the reactor system of FIG. 2, showing a reactor inlet assembly and reactor feed assembly constructed in accordance with particular embodiments of the invention.

Referring to FIG. 3, one or more or all of the flow spaces 72, 74, 80, 82 may be provided with a plurality of circumferentially spaced guide vanes 104, 106, 108, 110 (e.g., 10 to 60 guide vanes). Each guide vane 104, 106, 108, 110 may be a planar member that is oriented in a plane that is parallel to the central axis 52 and extends between the walls 60, 62, 64, 66, and 78. The guide vanes 104, 106, 108, 110 may be circumferentially spaced an equal distance from one another. In certain embodiments, the guide vanes 104, 106, 108, 110 may be fixed in place, with the upper and lower side edges of the guide vanes being joined along their lengths or a portion of their lengths to the walls 60, 62, 64, 66, and 78 so that there are no air gaps between the side edges of the vanes 104, 106, 108, 110 and the walls 60, 62, 64, 66, and 78. In other embodiments, however, the guide vanes are movable. In such cases, the upper and lower side edges of the vanes 104, 106, 108, 110 may be closely spaced from the walls 60, 62, 64, 66, and 78 to provide a small clearance to allow such movement but that minimizes air gaps where gases may pass through. Seals may also be used to effectively close these spaces or clearances while allowing movement. In other instances, the vanes 104, 106, 108, 110 may be oriented so that the plane of the vane is in a non-parallel or slanted orientation relative to the central axis 52. In such cases, the side edges may be fixed to the walls 60, 62, 64, 66, and 78 or remain closely spaced from walls 60, 62, 64, 66, and 78 to minimize air gaps for gasses to pass through. In certain applications, the guide vanes 104, 106, 108, 110 may be configured as airfoils, such as National Advisory Committee for Aeronautics (NACA) airfoil shapes, as described in E. N. Jacobs, K. E. Ward, & R. M. Pinkerton, NACA Report No. 460, "The characteristics of 78 related airfoil sections from tests in the variable-density wind tunnel" (NACA, 1933). The guide vanes may have curved surfaces, which may be oriented with the width being parallel or non-parallel to the axis 52, to provide desired flow characteristics, such as reduced drag and pressure drop. An example of a suitable airfoil design for the vane is discussed later in more detail.

The guide vanes 104, 106, 108, 110 are provided adjacent to the outer perimeter of the flow spaces 72, 74, 80, 82 and are spaced in an annular or circular ring pattern near the manifold inlets 96, 98, 100, 102, respectively, although they may be provided in an annular pattern at other positions located radially inward or further within the interior of the flow spaces 72, 74, 80, 82, or one or more additional annular sets of guide vanes may be located radially inward from those located along the outer periphery to facilitate inwardly swirling fluid flow.

Feed gases from the manifolds 88, 90, 92, 94 are delivered nearly tangentially to the outer perimeter of the flow spaces 72, 74, 80, 82, where the guide vanes 104, 106, 108, 110 further facilitate directing the gas flow in an inwardly swirling or spiraling fluid flow pattern within the flow spaces 72, 74, 80, 82. In other embodiments, the guide vanes 104, 106, 108, 110 may impart the full tangential flow of the introduced gases in cases where the gas from inlets 96, 98, 100, 102 may be directed radially toward the central axis 52. In such cases the guide vanes 104, 106, 108, 110 prevent flow directly toward the central axis 52 and direct the flowing gases tangentially to provide the inwardly swirling or spiraling fluid flow pattern.

The guide vanes 104, 106, 108, 110 of each flow space 72, 74, 80, 82 may be mounted on actuators (not shown) so that they can be selectively movable to various positions to provide a selected inwardly spiraling flow pattern. The guide vanes 104, 106, 108, 110 may be pivotal about an axis that is parallel to the central axis 52 so that the vanes 104, 106, 108, 110 may be moved to various positions.

The orientation of the vanes 104, 106, 108, 110, as well as the orientation of the tangential inlets 96, 98, 100, 102 may be seen in FIG. 4. As shown, the line 112 represents the angle of orientation of the vanes 104, 106, 108, 110 and/or inlets 96, 98, 100, 102 with respect to the radial line 114 extending radially from the central axis 52. Angle A is the angle between the tangential line 112 and the radial line 114. For non-planar vanes, such as airfoils, the line 112 may correspond to or represent a chord line passing through the leading edge and trailing edge of the vane or airfoil. In particular embodiments, the angle A may range from 50° to 90°, more typically from 60° to 85°. Thus, the vanes 104, 106, 108, 110 may be permanently oriented at an angle A within this range or may be movable to various angular orientations within this range. In most cases, each of the vanes 104, 106, 108, 110 within the annular pattern will be set at the same angle A and when actuated will move in unison or close to unison to the same angle A to provide the desired swirling fluid flow characteristics. The angle(s) of orientation A of the vanes 104, 106, 108, 110 and/or inlets 96, 98, 100, 102 of the different flow passages may be the same or different than the angle(s) of orientation of the vanes or inlets of the others.

In most cases, the tangential gas inlets 96, 98, 100, 102 and/or the guide vanes 104, 106, 108, 110 will be oriented to provide swirling or spiraling fluid jet flow that is in the same rotational direction about the axis 52, i.e., clockwise or counter-clockwise. Thus, gases within each of the flow spaces will flow clockwise or counterclockwise about the axis 52.

Referring again to FIG. 2, the area extending from the central openings 68, 70 of the partition walls 62, 70, respectively, to the reactor inlet 56 define a central mixing chamber 116. It is here that heated combustion gases from the flow space 76, hydrocarbon cracking feed from the upstream hydrocarbon feed inlet flow space 72, and steam from flow space 74 are discharged into the central chamber 116 so that hydrocarbon cracking feed, steam and heated combustion gases are mixed together and form a swirling gas mixture within the chamber 116. This swirling gas mixture then passes through the converging conduit 48 and into the reaction chamber 40 of the reactor vessel 36.

Because the oxygen-containing gas and hydrogen-rich fuel gas are introduced separately from one another into the flow spaces 80, 82, respectively, and not as mixture, this eliminates safety issues that would otherwise occur if these gases were premixed prior to their introduction into the feed assembly 58. Furthermore, the combustion reaction takes place very rapidly wherein most of the combustion occurs within a very small space within the combustion zone 86 where the two streams of oxygen-containing gas and hydrogen-rich fuel gas from the flow spaces 80, 82 are mixed immediately adjacent to the central opening 84 and prior to entering the chamber 116. The combustible mixture can be ignited through spark or chemicals or pilot flame through bottom surface or side surfaces of the reactor as the suction from the strong swirling flow (that mimics a tornado) will transport the hot gases from the ignition device to the combustion zone 86 to initiate the ignition.

Referring to FIG. 2, in operation, a cracking feed is introduced from manifold 88 to tangential inlets 96A, 96B into flow space 72. The cracking feed may be ethane, LPG, butane, naphtha, natural gas, light gas oils, heavy gas oils, or their combinations. While these cracking feed materials are typically introduced as gases, in some instances they may be introduced as liquids. Once introduced as liquids they are rapidly vaporized within the reactor. This may be beneficial in that light and heavy gas oils, for example, are typically vaporized outside the reactor in conventional cracking systems. Such exterior vaporization creates coking issues, however. By injecting them directly into the reactor in liquid form, these issues are avoided. The cracking feed will typically be denser than the combustion products. This is a result of both the high molecular weight of the cracking feed and its density at the selected temperature of the cracking feed. The denser gas/liquids move outward while the lighter combustion products move inward due to very high centrifugal acceleration (100,000-1 M g forces). The denser hydrocarbons rapidly mix into the peripheral combustion products at very high temperature due to high swirl.

A hydrogen-containing fuel gas is introduced from manifold 94 to tangential inlets 102A, 102B into flow space 82. The hydrogen-containing fuel gas may be hydrogen gas ($H_2$) and/or methane ($CH_4$). In certain embodiments where a combination of hydrogen gas and methane are used, the methane may be present in the fuel gas in an amount of from 20 mol %, 15 mol %, 10 mol %, 5 mol % or less. Greater amounts of methane may impact the desired selectivity. In other embodiments, however, greater amounts of methane may be used, including 100% methane for the fuel gas. Natural gas may also be used as the fuel gas.

The hydrogen-containing fuel gas may be a hydrogen-gas-rich stream composed primarily of hydrogen gas, which may be a recycled stream such as the recycle stream 32 (FIG. 1) or additional hydrogen gas, such as the stream 34. The hydrogen-gas-rich stream may contain other components such as methane, CO, steam, inert gases, and $CO_2$. Other hydrocarbons can also be used as the fuel gas in certain embodiments and applications. Additionally, small amounts of $N_2$ can also be present. Sulfur can also be present in the fuel gas or other feed streams. If sulfur is present, additional separation upstream or downstream may be required. The reactor and process are sufficiently robust to accommodate the presence of sulfur, particularly since no catalyst is used. The ratio between the crack feed to hydrogen-containing fuel will typically range from 1 to 15, more particularly from 1 to 10, based on mass.

An oxidizer or oxygen-containing gas, which may be a concentrated or pure oxygen gas, such as from an air separation unit (not shown), is introduced as the oxidizer feed through manifold 92 through inlets 100A, 100B into the flow space 80. Having the oxygen-containing gas introduced through flow space 80 spaces it further from the cracking gas introduced through flow space 72 to eliminate or minimize any combustion of the introduced cracking gas. In certain applications, the mole ratio of $H_2/O_2$ may range from 2 to 9, more particularly from 2 to 5, and still more particularly from 2 to 4. The oxygen feed may provide an oxygen equivalent-to-fuel mole ratio of from 0.2 to 1.0. An excess of hydrogen also helps to scavenge free radicals (e.g., O, OOH, OH) formed that would otherwise react with the cracking feed. In some cases, a mole ratio of $H_2/O_2$ may be less than 2 to compensate for other fuel gases or to have excess $O_2$ in the mixing region to release heat to counter endothermic cracking reactions.

Steam or water is introduced through manifold 90 and through inlets 98A, 98B into the flow space 74. Steam is introduced upstream of the other feeds and is used to cool the walls of the converging conduit 48 and reactor 12. The introduced steam also facilitates reducing the reaction temperatures within the reactor 12. Steam may also be premixed with the various feeds, such as with the cracking gas feed, fuel gas, and/or oxygen-containing feed. Steam may be used in a mass ratio of steam-to-fuel of from greater than 0 to 10.0, more particularly from 0 to 2.0, in certain applications.

Figure 5:
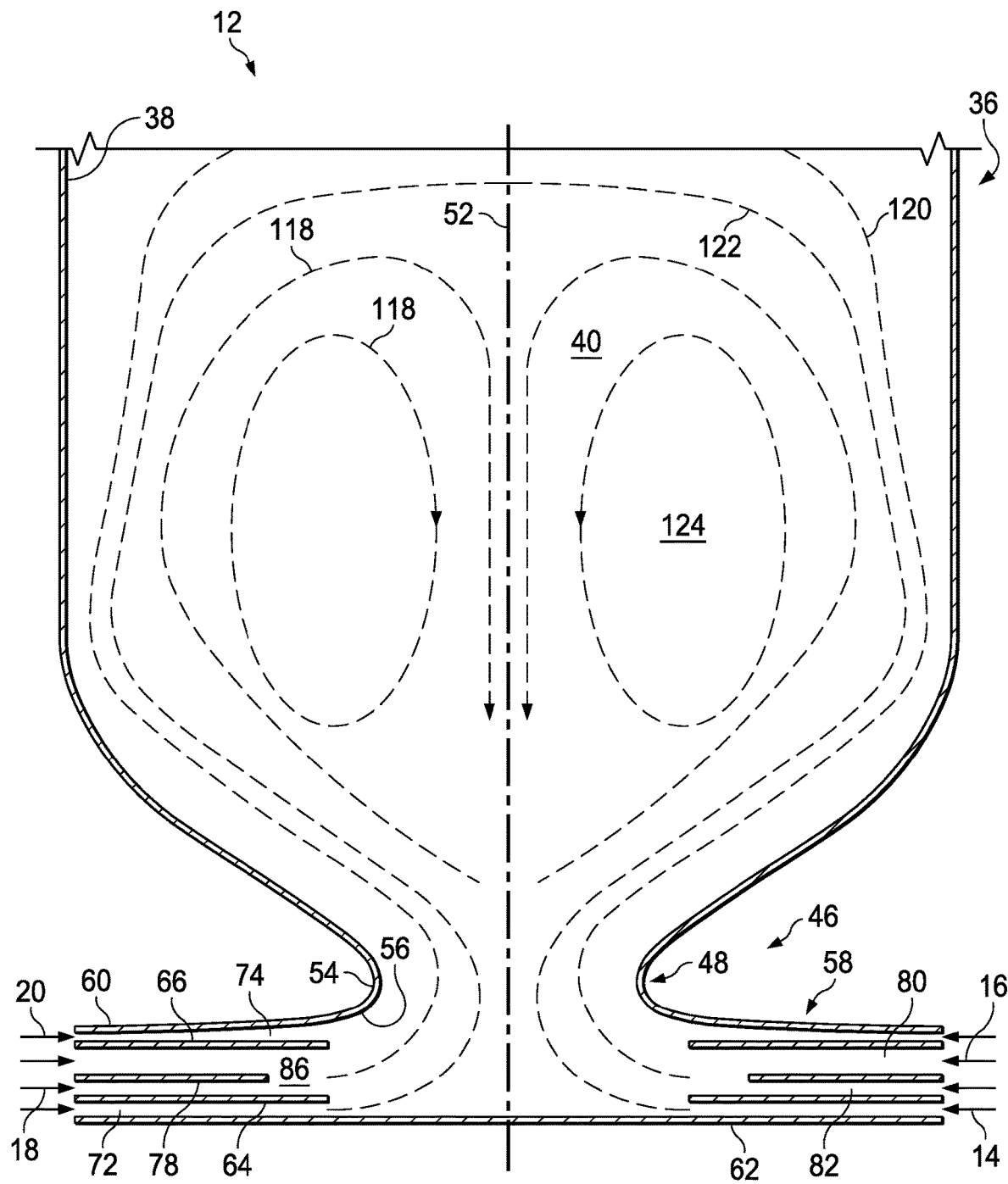
FIG. 5 is a schematic of the cracking reactor system of FIG. 2 showing gas flows within the reactor.

FIG. 5 shows a schematic diagram of the reactor 12 with the individual flows of the different feeds. These individual flows are schematically represented by dashed lines. In actual practice, all of the oxygen gas and at least a portion of the hydrogen-containing fuel gas are combusted to form heated combustion products that are almost entirely mixed with the other feeds prior to exiting the converging conduit 48 and entering the reaction chamber 40. Thus, while the individual feeds are schematically shown by the dashed lines, the gases flowing into the reaction chamber 40 constitutes a gas mixture. With the high centrifugal force of the swirling gases, the denser gases (e.g., cracking feed) flow closer to the reactor wall, while the hotter combustion products tend to flow through the center of the reactor. The device geometry and the swirling gas-mixture from chamber 116 results in a back flow of the gas mixture as represented by dashed lines 118. This mixture flows upstream and radially inward from the thin, outer annular mixed gas flow layers 120, 122, circulating within the reaction chamber 40 to form recirculation zone 124. Internal cooling of the walls occurs due to the high swirling steam delivered through flow space 74 in FIG. 2. Additional cooling (if necessary) occurs by a water jacket located between walls 38 and 42 in FIG. 2.

The gas feed streams may be introduced to provide different flow velocities to provide the Kelvin-Helmholtz instability for enhanced mixing. The flow velocities may range from 10 m/s to 500 m/s, more particularly from 100 m/s to 400 m/s. The reactor may be operated at from 0 kPa (g) or 100 kPa (g) to 1,000 kPa (g), 2,000 kPa (g) or as much as 10,000 kPa (g), with a gas residence time within the reactor of from 50 milliseconds or less, more particularly from 20 milliseconds or less, and still more particularly from 10 microseconds to 20 milliseconds. In particular embodiments, the residence time may range from 20, 19, 18, 17, 16, 15, 14, 13, 12, 11, or 10 milliseconds or less, with 10 microseconds being the approximate lowest residence time.

The reaction temperature within the reactor and recirculation zone 124 may range from 900° C. to 1300° C. In particular embodiments, the temperature within the reactor and recirculation zone 124 may range from 1000° C. to 1300° C., more particularly from 1200° C. to 1250° C. In some embodiments, the reactor temperature is higher than what is achieved in conventional cracking reactors, such as tube furnace reactors, which typically operate at 800° C. to 900° C. As discussed earlier, this is due to the temperature limitations of the metallic materials used for such conventional reactors. In the present case, the swirling gas mixture facilitates keeping the walls of the reactor much cooler than in such conventional reactors. The use of such higher temperatures also allows a shorter residence or contact times shorter contact times resulting in better selectivity and conversion without formation of unwanted products. Operating temperatures for the reactor may be selected to avoid excess production of such unwanted compounds, such as acetylene.

The gases are introduced and flow through the flow spaces 72, 74, 80, 82 so that the axial velocity (i.e., relative to the axis 52) is zero prior to being discharged into the mixing chamber 116. The tangential inlets 96, 98, 100, 102 and/or the orientation of the guide vanes 104, 106, 108, 110 may be set for each flow space 72, 74, 80, 82 so that a selected azimuthal-to-radial velocity for each of the feed streams that flow through the flow spaces 72, 74, 80, 82 is achieved. With respect to the azimuthal-to-radial velocity, in particular embodiments, this may range from 0 to 30 or more, more particularly from 0, 1, or 2 to 3, 4, 5, 6, 7, 8, 9, 10, 11, 12, 13, 14, 15, 16, 17, 18, 19, 20, 21, 22, 23, 24, 25, 26, 27, 28, 29, or 30. In some applications the azimuthal-to-radial velocity may range from 0 to 5, more particularly from 2 to 4. The particular azimuthal-to-radial ratio may vary depending upon the particular reactor configuration and composition of the various streams, however. This is more intimately related to the mixing times and reaction times depending on the flow rates, composition of the fuel and feedstocks used for cracking.

Cracked hydrocarbon products produced in the reactor are removed from the reactor vessel 36 through outlet 44, where they may be quenched and further processed and recycled, as discussed with respect to the process steps previously described for FIG. 1.

In a variation of the reactor described, additional cracking feed gas can be introduced as a secondary feed stream at an intermediate position along the length of reactor vessel 36, such as at inlet 126 (FIG. 2). One or more such inlets 124 may be provided at various locations and in the reactor vessel 36, which may be circumferentially and longitudinally spaced apart. The inlets 126 may be oriented or configured so that gases are introduced tangentially, as well, to facilitate swirling fluid flow, similar to that delivered from the inlets of the feed assembly 58. Feed assemblies provided on the reactor vessel 36 similar to the feed assembly 58 may be used for the introduction of such cracking feed gas so that the cracking feed is introduced as a swirling fluid flow.

In some embodiments, a plurality of reactor inlet assemblies and corresponding feed assemblies can be provided in a single reactor while maintaining the high performance.

Figure 6:
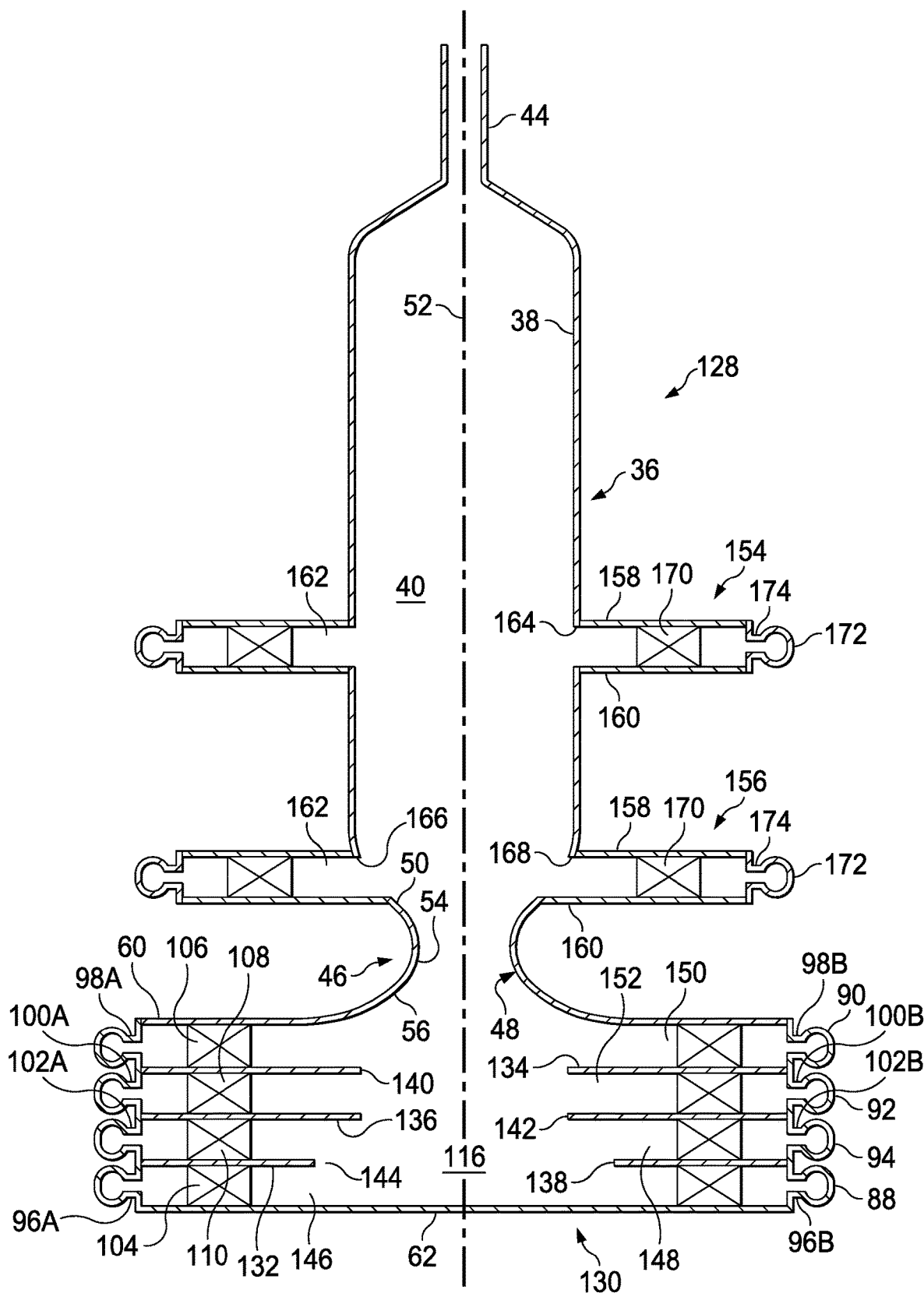
FIG. 6 is schematic representation of an alternate embodiment of a reactor system for cracking hydrocarbons shown in cross section and constructed in accordance with particular embodiments of the invention.

Referring to FIG. 6, an alternate embodiment of a reactor 128 is shown. The reactor 128 is similar to reactor 12, previously described, with similar components labeled with the same referenced numerals. The reactor 128 includes a reactor feed assembly 130, which is similar to the feed assembly 58 previously described with some differences with respect to the partition walls located between the downstream feed assembly wall 60 and the upstream feed assembly wall 62.

As shown in FIG. 6, the feed assembly 130 has an upstream gas partition wall 132 and a downstream gas partition wall 134 that are axially spaced between the downstream and upstream feed assembly walls 60, 62. An intermediate partition wall 136 is axially spaced between the upstream gas partition wall 132 and the downstream gas partition wall 134, with the partition walls 132, 134, 136 being axially spaced from one another. The partition walls 132, 134, 136 or circumferential portions thereof are also each oriented perpendicularly to or substantially perpendicularly (i.e., ≤5 degrees from perpendicular about its circumference as it extends radially from the central axis) to the central axis 52. Each of the partition walls 132, 134, 136 terminates at their inner ends at a position below or upstream of the converging conduit 48 to define central openings 138, 140, 142, respectively, that surrounds the central axis 52 and are concentric with the converging conduit 48. The central openings 138, 140, 142 each have a circular configuration. Other shapes for the central openings 138, 140, 142 (e.g., oval) may also be used provided such configuration facilitates the swirling of gases to provide the required flow patterns described herein. This shape may also correspond to the cross-sectional shape of the circumferential wall 50 of the converging conduit 48. In most applications, however, the central openings 138, 140, 142 will be circular in shape. The central openings 138, 140, 142 may have a diameter or width that is the same or slightly different than the diameter or width of the constricted neck 54 of the converging conduit 48 at its narrowest point.

In the reactor 128, the central opening 138 of the upstream partition wall 132 may have a periphery that is spaced radially outward a distance from the central opening 142 of the intermediate partition wall 136, as is shown. The area spaced radially inward from the central opening 142 of the intermediate partition wall 136 between the upstream feed assembly wall 62 and the intermediate partition wall 136 defines an annular combustion zone 144. The size of the central opening 138 can vary to fit the radial extent of combustion zone 144.

The upstream partition wall 132 is axially spaced between the upstream feed assembly wall 62 and the intermediate partition wall 136 to define flow spaces 146, 148 which constitute first and second annular fuel gas inlet flow spaces. In the embodiment shown, the flow space 146 constitutes an upstream annular fuel gas feed inlet flow space and the flow space 148 constitutes a downstream annular fuel gas feed inlet flow space. The fuel gas feed may be comprised of an oxygen-containing fuel gas feed and a hydrogen-rich fuel gas feed, as described previously, that are introduced into the first and second annular fuel gas inlet flow spaces 146, 148, as with reactor 12. In many applications, the flow space used for the oxygen-containing will be spaced furthest from the hydrocarbon cracking feed flow to prevent or minimize any combustion of the cracking feed. Thus, in the embodiment shown, the oxygen-containing gas would be introduced into flow space 146. Either of the oxygen-containing or hydrogen-rich fuel gases introduced into flow spaces 146, 148, or both, may be introduced with a steam cofed. An annular gas flow space 150 is defined by the downstream side of the downstream partition wall 134 and the downstream feed assembly wall 60. In the embodiment shown, the flow space 150 may constitute an annular hydrocarbon cracking feed inlet flow space or alternatively a steam feed inlet flow space.

A further annular flow space 152 is also defined between the upstream side of the downstream gas partition wall 134 and the downstream side of the intermediate partition wall 136. The flow space 152 may constitute an annular steam or water inlet flow space or alternatively an annular hydrocarbon cracking feed inlet flow space.

Where steam is cofed with the fuel feeds, a separate steam feed to the feed assembly 130 may be eliminated. In such cases, one of the flow spaces 150, 152 may be eliminated by the removal of either the partition walls 134, 136 and the intervening flow space.

The flow passages 146, 148, 150, 152 are configured so that the different feeds pass through flow spaces perpendicularly or substantially perpendicularly to the central axis 52 of the converging conduit 48 in an inwardly swirling fluid flow pattern within said flow spaces so that the feeds flow about the central axis 52 of the converging conduit 48. Guide vanes 104, 106, 108, 110 may also be used to facilitate swirling fluid flow. The fuel gas feed from flow combusts primarily in the small combustion zone 144 between the inner end of partition wall 136 and upstream feed assembly wall 62 within the central opening 138 of the upstream partition wall 132.

In the embodiment of FIG. 6, the oxidizing gas nears complete combustion in the combustion zone 144, located below the cracking feed introduced into one of the flow passages 150, 152. Therefore, the cracking gas meets only combustion products above the zone 144. Additionally, the cold flow of the incoming cracking gas in the flow passage 150 or 152 moderates the temperature of the circumferential wall 50 of conduit 48 as it flows through the reactor inlet 46 and also protects the reactor walls 38 from overheating.

The reactor 128 also differs from the reactor 12 in that the wall 42 (FIG. 2) for the cooling jacket is eliminated. To facilitate cooling of the reactor 28 one or more cooling gas feed assemblies 154, 156 are provided for introducing or injecting cooling gases into the reactor 128. The cooling gases may be a neutral or inert gas, such as steam, which may be at a temperature sufficient to provide the desired cooling effect. This may include steam at a temperature of from 100° C. to 250° C. (e.g., 150° C.). The cooling gas can also be hydrocarbon cracking feed at a relatively lower temperature, for example from 25° C. to 500° C.

The cooling gas feed assemblies 154, 156 may be configured similarly to the feed assemblies 58, 130 of the reactors 12 and 128 to provide a swirling flow of cooling gases as they are introduced into the reactor 128. Each cooling gas feed assembly 154, 156 is constructed from a pair of axially spaced apart cooling gas feed assembly walls 158, 160 oriented perpendicular or substantially perpendicular (i.e., ≤5 degrees from perpendicular about its circumference as it extends radially from the central axis) to the central axis 52.

An annular cooling gas inlet flow space 162 is defined between the cooling gas feed assembly walls 158, 160 of each cooling gas feed assembly 154, 156. In the embodiment shown, the cooling gas feed assembly 154 constitutes a downstream cooling assembly with the inlet flow space 162 communicating with a circumferential opening or inlet 164 of the reactor wall 38 and the reaction chamber 40. The position of the feed assembly 154 and inlet 164 may be located at a position along the length of the reactor wall 38 or cylindrical portions of the reactor wall 38 above the contoured, concave or tapered portion 166 and above the reactor inlet assembly 46 and converging conduit 48.

The cooling gas feed assembly 156 constitutes an upstream cooling assembly with the inlet flow space 162 communicating with a circumferential opening or inlet 168 of the reactor wall 38 or circumferential wall 50 along the contoured, concave or tapered portion 166 where the reactor wall 38 and circumferential wall 50 of the converging conduit 48 meet.

Each of the annular flow spaces 162 of the cooling gas feed assemblies 154, 156 may also be provided with a plurality of circumferentially spaced guide vanes 170 to facilitate swirling fluid flow within the cooling gas inlet flow spaces 162 of the feed assemblies 154, 156. The guide vanes 170 may be constructed and operate similarly to the guide vanes 104, 106, 108, 110, previously described.

An annular cooling gas manifold 172 may be provided around the outer periphery of the flow spaces 162 of each of the feed assemblies 154, 156. The gas manifold 172 is fluidly coupled to a cooling gas feed source, such as steam. Cooling gas inlets 174 of the manifold 172 may be directed tangentially into the flow space 162 so that the cooling gases are not directed radially toward the central axis 52, but instead are directed mostly tangentially around the central axis 52 to provide an inwardly swirling flow pattern. Furthermore, the walls 158, 160 forming the flow spaces 162 of the cooling gas feed assemblies 154, 156 keep the cooling gases introduced from the manifold 172 from flowing axially along the central axis 52 while they are contained within the flow spaces 162. The manifolds 172 can be configured as standard manifolds (e.g., snail-like) as may be typically used in vortex devices.

The high swirl velocity and comparatively low temperature of the injected cooling gases presses the cooling gases along the sidewalls of the reactor. The cooling effect allows the elimination of a cooling jacket and/or the use of refractory materials for the reactor 128.

In certain embodiments, several cooling gas feed assemblies, such as the feed assemblies 154, 156, may be provided as necessary along the length of the reactor 128 to facilitate sufficient cooling. Likewise, either one of the feed assemblies 154, 156 may be eliminated in certain embodiments.

Figure 7:
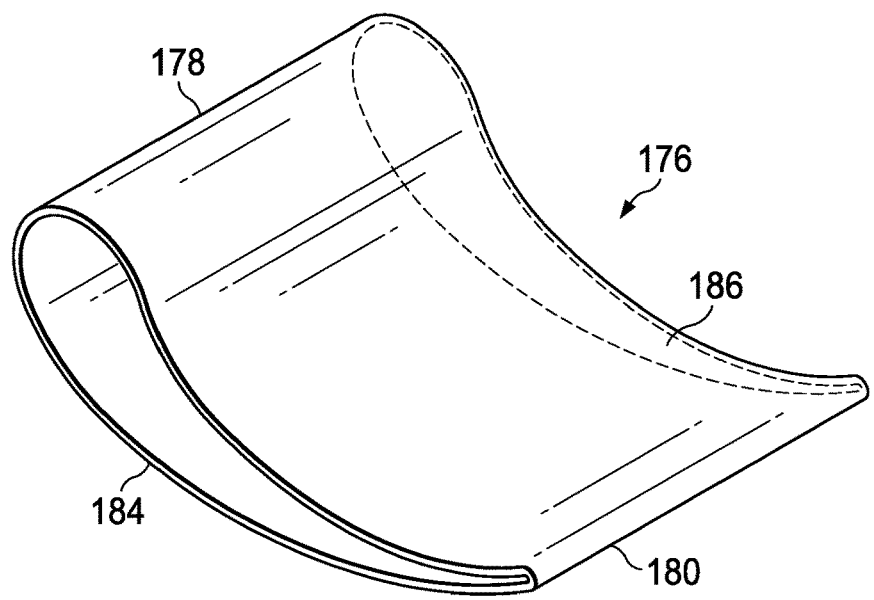
FIG. 7 is a perspective view of an airfoil for use in the reactor feed assemblies described herein.

Referring to FIG. 7, a vane 176 that may be used for any one or all of the feed assemblies 58, 136, 154, 156. The vane 176 is non-planar and is configured as an airfoil. The vane 176 is configured to reduce drag and includes a leading end 178 and trailing end 180.

Figure 8:
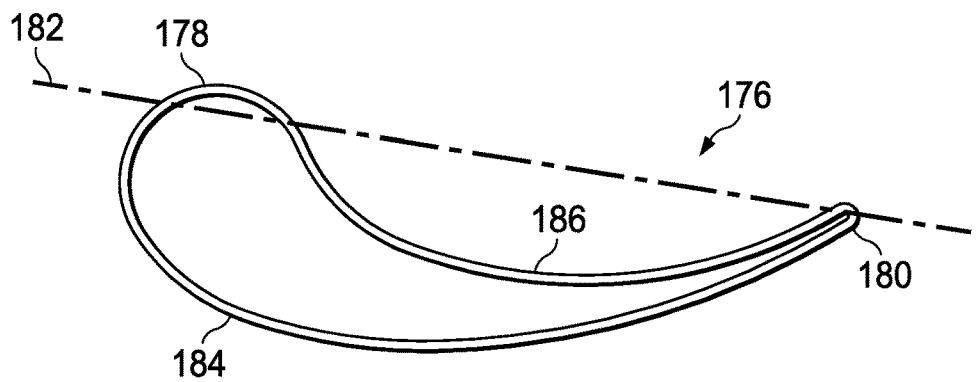
FIG. 8 is a top plan view of the airfoil of FIG. 7.
Figure 9:
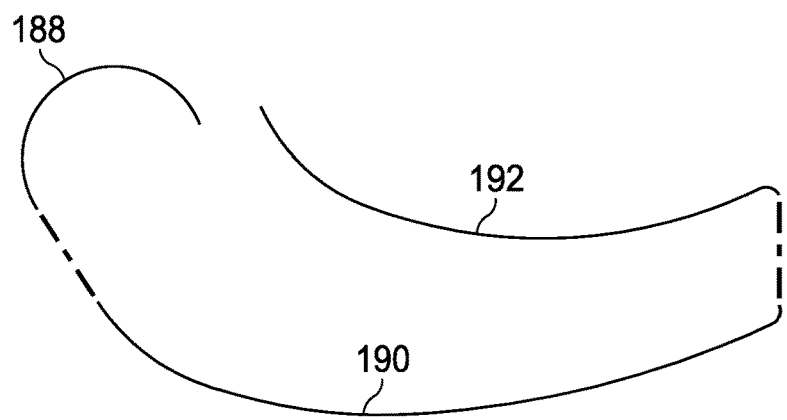
FIG. 9 is a schematic diagram of the three different arcs used in forming the airfoil of FIG. 7.

FIG. 8 shows a top plan view of the airfoil vane 176. A chord or line 182 passing through the leading edge and trailing edge of the vane 176 may correspond to the line 112 of FIG. 4. The leading end 178 and trailing end 180 are joined by opposite sidewalls 184, 186 that converge at the trailing end 180. The transverse dimensions of the vane 176 may be uniform along the height of the vane. In other embodiments, however, the transverse dimensions may vary along the height of the vane. As shown in FIG. 9, the curved sidewalls of the airfoil 176 may be represented by three arcs 188 190, and 192, which are shown exploded away from one another. The arc 188 represents the leading end or leading end wall or cap of the vane 176. The arc 190 constitutes a left arc representing the left sidewall 184 that joins the leading arc 184 at one end and terminates at the other end at the trailing end 180 of the airfoil 176. The arc 192 constitutes a right arc representing the right sidewall 186 that joins the leading arc 184 at one end and terminates at the other end at the trailing end 180 of the airfoil 176.

Figure 10:
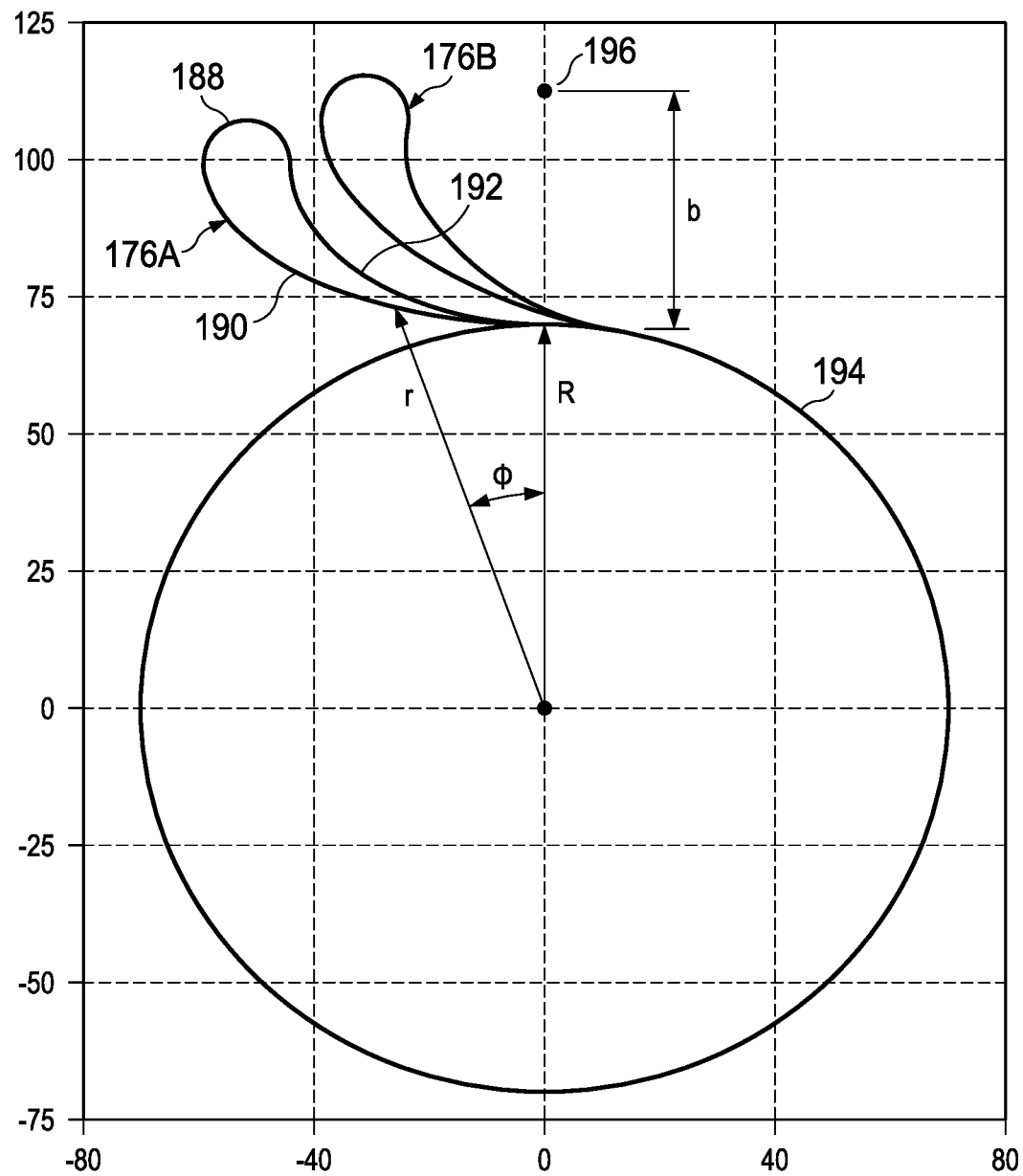
FIG. 10 is a diagram showing a pair of airfoils as arranged in a circular pattern to demonstrate the configuration and location of the circumferentially spaced airfoils as they may be used with those reactor feed assemblies described herein.

Referring to FIG. 10, a schematic showing a pair of airfoil vanes 176A and 176B as they would be arranged within any one of the flow spaces of the gas inlet feed assemblies as has been previously described. As can be seen, the trailing ends 180 are arranged around the perimeter of a circle 194 having a radius R, which defines the inner boundary of the gas vanes 176. Points on the vanes 176A, 176B can be determined by the polar coordinates r and $\phi$. The points on the vanes 176A, 176B can also be presented by the Cartesian coordinates $x=r\cdot\cos(\phi)$ and $y=r\cdot\sin(\cdot)$).

To design the airfoil 176A, the arc of an ellipse having a center 196 located at $x_e=0$, and $y_e=R+b$ can be used. The left arc 190 can be described by the equations $(x/a)^2 + ((y-y_e))^2 = 1$, $-a<x<0$, and $y<y_e$, $a=k_1R$, $b=a/2$. As an example, $k_1$ can equal 0.85.

The right arc 192 is essentially the left arc 190 compressed to the y axis. Here, the right arc 192 can be defined by $x_R = k_2 x_L$ where $y_R = y_L$. As an example, $k_2$ can equal 0.75. The equation describing the leading arc 188 is the upper half of a circle $((x-x_e)/R_2)^2 + ((y-y_e)/R_2)^2 = 1$, $y>R+b$, where $x_e = k_1R(1+k_2)/2$ and $R_2 = k_1R(1-k_2)/2$. These three arcs 188, 190, 192 together constitute the left guide vane 176A.

In order to represent the right vane 176B, each point for the left vane 176A (i.e., $x_1$, $y_1$), its polar coordinates $r_1 = (x_1^2 + y_1)^{1/2}$ and $\phi_1 = a\cdot\cos(x_1/r_1)$ are calculated. Then the polar angle, $\phi_2 = \phi_1 - 2\pi/N$ is calculated, where N is the total number of circumferentially-spaced guide vanes within the flow space. The Cartesian coordinates of the right vane 176B can be calculated as $x_2 = r_1 \cdot \cos(\phi_2)$ and $y_1 \cdot \sin(\phi_2)$.

The procedure of calculating the right vane 176B can be repeated until all guide vanes are represented. The control parameters R, N, $k_1$, and $k_2$ can be modified for specific applications.

Figure 11:
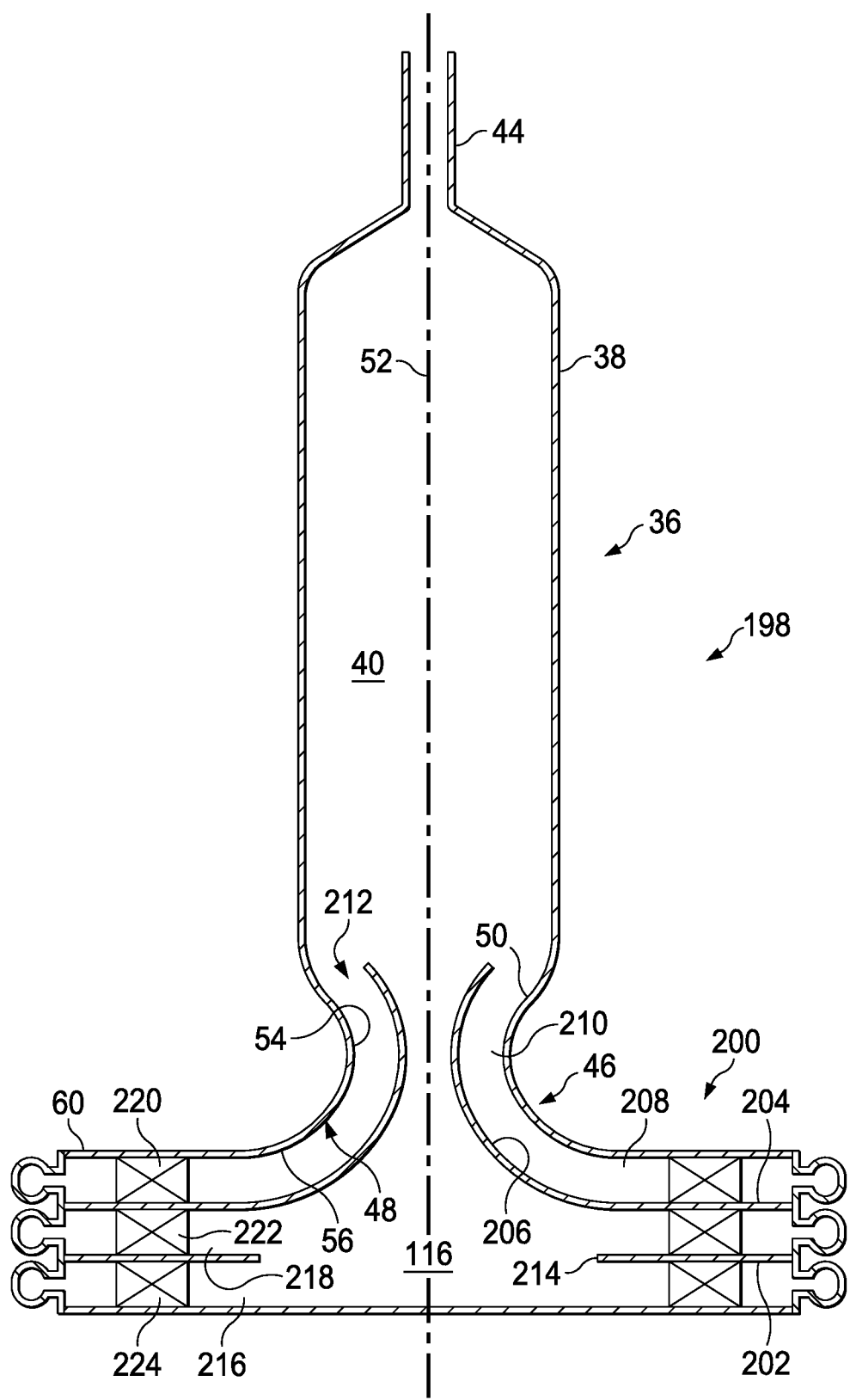
FIG. 11 is schematic representation of another embodiment of a reactor system for cracking hydrocarbons shown in cross section and constructed in accordance with particular embodiments of the invention.

FIG. 11 shows another embodiment of a reactor 198 is shown. The reactor 198 is similar to the reactors 12 and 128, previously described, with similar components labeled with the same referenced numerals. The reactor 198 includes a reactor feed assembly 200, which is similar to the feed assemblies 58, 130 previously described with some differences.

The feed assembly 200 has an upstream gas partition wall 202 and a downstream gas partition wall 204 that are axially spaced between the downstream and upstream feed assembly walls 60, 62. An upstream partition wall 202 is axially spaced between the upstream gas feed assembly wall 62 and the downstream gas partition wall 204, with the partition walls 202 and 204 being axially spaced from one another. The partition walls 202, 204 or circumferential portions thereof are also each oriented perpendicularly to or substantially perpendicularly (i.e., ≤5 degrees from perpendicular about its circumference as it extends radially from the central axis) to the central axis 52.

As shown in FIG. 11, the downstream gas partition wall 204 differs from those previously described in that extending from the downstream partition wall 204 is a curved annular extended wall portion 206 that curves upward or downstream and is spaced from and follows the contours of the circumferential wall 50 of the converging conduit 48 of the reactor inlet assembly 46 and terminates at a position downstream of the annular constricted neck portion 54. The partition wall 204 with the extended curved portion 206 defines a downstream inlet flow space 208 located in the annular space between the downstream feed assembly wall 60 and circumferential wall 50 of the reactor inlet assembly 46 and the partition wall 204 with the extended portion 206. A curved portion 210 of the downstream inlet flow space 208 discharges at a central annular opening 212 that surrounds the central axis 52 into the reactor chamber 40 downstream from the constricted neck portion 54.

The upstream partition wall 202 terminates at its inward end at a position upstream from the converging conduit 48 and has a central opening 214 that surrounds the central axis 52 and is concentric with the converging conduit 48. The central opening 214 has a circular configuration. Other shapes for the central opening 214 (e.g., oval) may also be used provided such configuration facilitates the swirling of gases to provide the required flow patterns described herein. This shape may also correspond to the cross-sectional shape of the circumferential wall 50 of the converging conduit 48.

The upstream partition wall 202 is axially spaced between the upstream feed assembly wall 62 and the downstream partition wall 204 to define flow spaces 216, 218 which constitute first and second annular fuel gas inlet flow spaces. In the embodiment shown, the flow space 216 constitutes an upstream annular fuel gas feed inlet flow space and the flow space 218 constitutes a downstream annular fuel gas feed inlet flow space. The fuel gas feed may be comprised of an oxygen-containing fuel gas feed and a hydrogen-rich fuel gas feed, as have been described previously, that are introduced into the first and second annular fuel gas inlet flow spaces 216, 218. Either of the oxygen-containing or hydrogen-rich fuel gases introduced into flow spaces 216, 218, or both, may be introduced with a steam cofed. In the embodiment shown, the flow space 208 may constitute an annular hydrocarbon cracking feed inlet flow space.

The flow passages 208, 216, 218 are configured so that the different feeds initially pass through flow spaces perpendicularly to the central axis 52 of the converging conduit 48 in an inwardly swirling fluid flow pattern within said flow spaces so that the feeds flow about the central axis 52 of the converging conduit 48. Guide vanes 220, 223, 224 may be used to facilitate such swirling flow.

In the case of the cracking gas introduced through flow space 208, the cracking gas flows spirally upward through the curved portion 210 of the flow space 208 and is discharged through opening 212 into the reaction chamber.

The fuel gas feed from flow spaces 216, 218 combusts in the central chamber 116. Because the downstream partition wall 204 has an extended portion 206 that extends past the constricted neck portion 54 and separates the combusting fuel gases within the central chamber 116 where they are fully combusted or the oxygen-containing gas is fully consumed there is no danger of the introduced cracking gas being combusted. The introduced cracking gas also facilitates cooling of the reactor walls.

The reactor designs described herein feature high conversion of the cracking feed and higher selectivity for olefins than other conventional cracking methods and at much higher pressures than typically used. The reactors are relatively simple in configuration, which can significantly reduce the capital and operating costs. The high-swirling gas mixture provides stable and compact combustion using non-premixed fuel gases (i.e., $H_2+O_2$) that are combusted within a small combustion zone of the feed assembly. The reactor walls are cooled by the swirling steam flow (or cooler feed) against the wall allowing for higher temperatures in the reactor, requiring shorter residence times, so that more desirable products (e.g., ethylene) are produced. Maintaining lower reactor wall temperatures also allows refractory materials to be used in place of metal materials and thus minimizing heat loss.

Because the heated combustion gases are directly mixed with cracking feed in the swirling gas mixture, there is direct gas-gas heat transfer to carry out the cracking reactions. This differs from conventional cracking reactors, such as tube furnaces, that rely on non-direct heat transfer where heat is transferred through the tube walls of the reactor from a separate heating source, such as external combustion gases. Here the process is intensified in that the exothermic step of providing heat from the combustion of the fuel feed is immediately combined with the endothermic step of cracking the cracking feed. Thus, energy losses due to heat transfer through reactor walls and equipment, as with conventional systems, are eliminated or minimized. The reactor can be scaled up by increasing feeding rate and dimension scale up.

The following examples serve to further illustrate various embodiments and applications.

EXAMPLES

Example 1

Computational Fluid Dynamics (CFD) simulations, using commercial software available as the ANSYS FLUENT® software product, were conducted for the optimal design of a cracking reactor, as has been described herein, to verify its performance by numerical experiments. The swirling fluid flow, heat transfer, and detailed gas phase reactions were modeled in a two-dimensional axisymmetric CFD framework using Reynolds Averaged Navier-Stokes (RANS) approach using Reynolds Stress turbulence model. The modeled base case ANJEVOC-C reactor had an inner diameter of about 6 inches. Ethane was used as the cracking feed. The feeds used were 72 kg/h ethane, 38 kg/h oxygen blending with 38 kg/h steam, 12 kg/h hydrogen, and another 18 kg/h steam stream near the wall of the reactor for wall protection. Based upon prior experience with similar reactors, one can scale this reactor to use 3600 kg/h ethane, 1800 kg/h oxygen blending with 1800 kg/h steam, 612 kg/h hydrogen, and another 900 kg/h steam stream near the wall of the reactor for wall protection.

Figure 12:
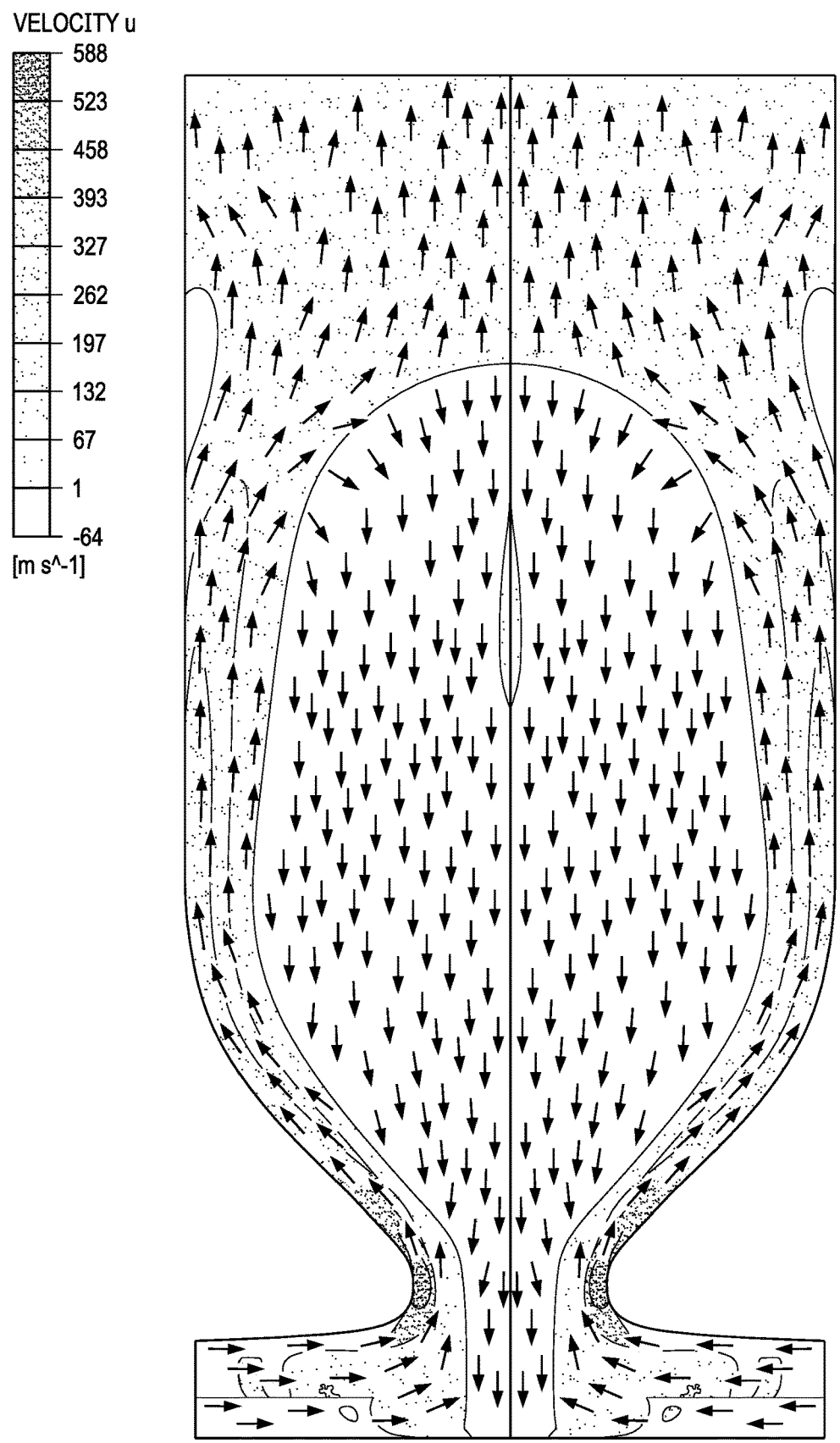
FIG. 12 is a representation of the cracking reactor geometry and axial velocity distribution of gas flow in a lab scale reactor unit model of Example 1.
Figure 13:
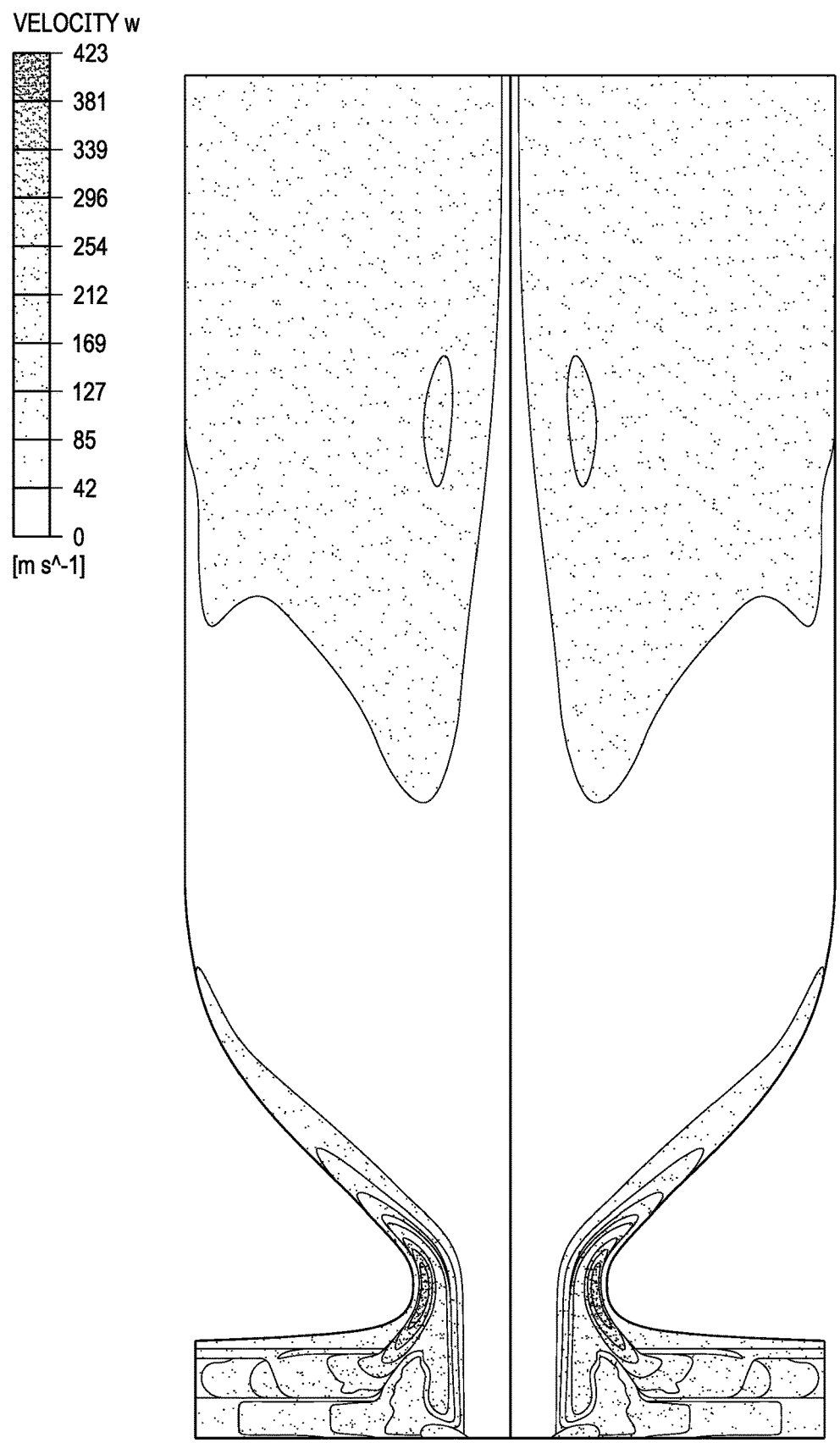
FIG. 13 is a representation of the cracking reactor geometry and swirl velocity distribution of gas flow in a lab scale reactor unit model of Example 1.

FIGS. 12 and 13 show the cracking reactor geometry and axial velocity and swirl velocity distribution in a lab scale unit model. The darker areas of FIG. 6 indicate a high axial velocity while the lighter areas indicate a low axial or negative (reverse flow) velocity relative to the longitudinal axis. Together with the axial velocity contour, arrows are presented on the same figure indicating flow directions. At the feed assembly inlet, the axial velocity was close to zero for each of the feeds, the radial and the azimuthal velocity were uniform, and the azimuthal-to-radial velocity ratio was 10 for all the inlet streams. This highly swirling flow forms a recirculation region near the axis of the reactor as described above with respect to recirculation zone 124 of FIG. 5. This can be seen by the lightest regions (reverse flow region in reaction chamber near the axis in FIG. 12). The highest axial flow regions were the darker areas along the converging conduit and along the reactor walls.

FIG. 13 shows the swirl velocity, with the darker regions representing higher swirl velocity and the lighter regions representing lower swirl velocity. As can be seen, the swirl velocity is greatest along the outer edges of the mixing chamber of the feed assembly, with the greatest swirl velocity being along the constricted neck portion of the converging conduit. The swirl velocity is also high along the sidewalls of the reactor where it joins the converging conduit.

Figure 14:
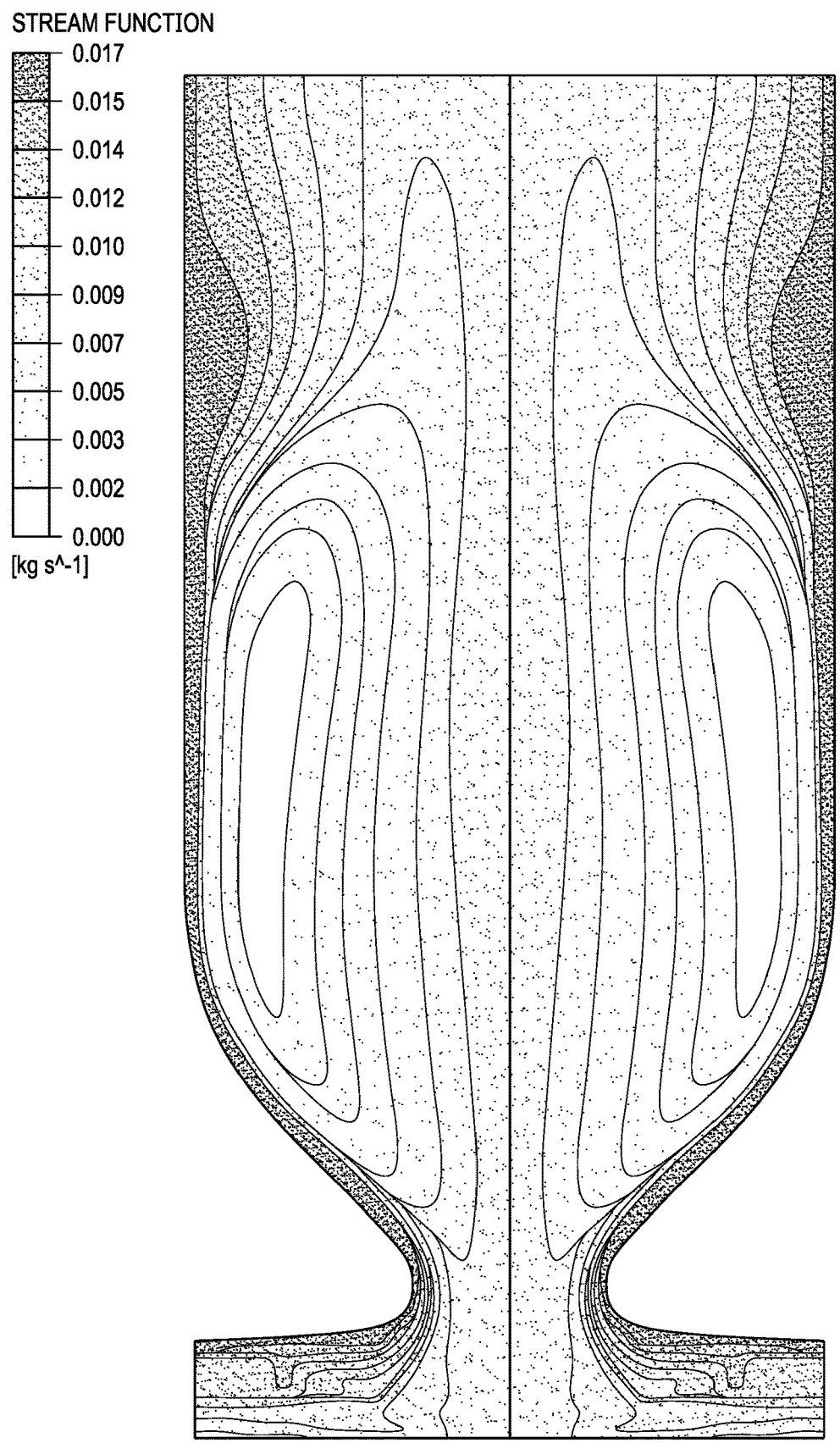
FIG. 14 is a representation of the meridional flow pattern (stream function contours) in the lab scale reactor unit of Example 1.

FIG. 14 shows the stream function. The through-flow goes near the reactor wall in the nozzle and the adjacent half of the cylindrical parts. There the reversed flow near the axis and the recirculation of mixed gases occurs between the axis and the wall. The curves separating gray scales are streamlines.

Figure 15:
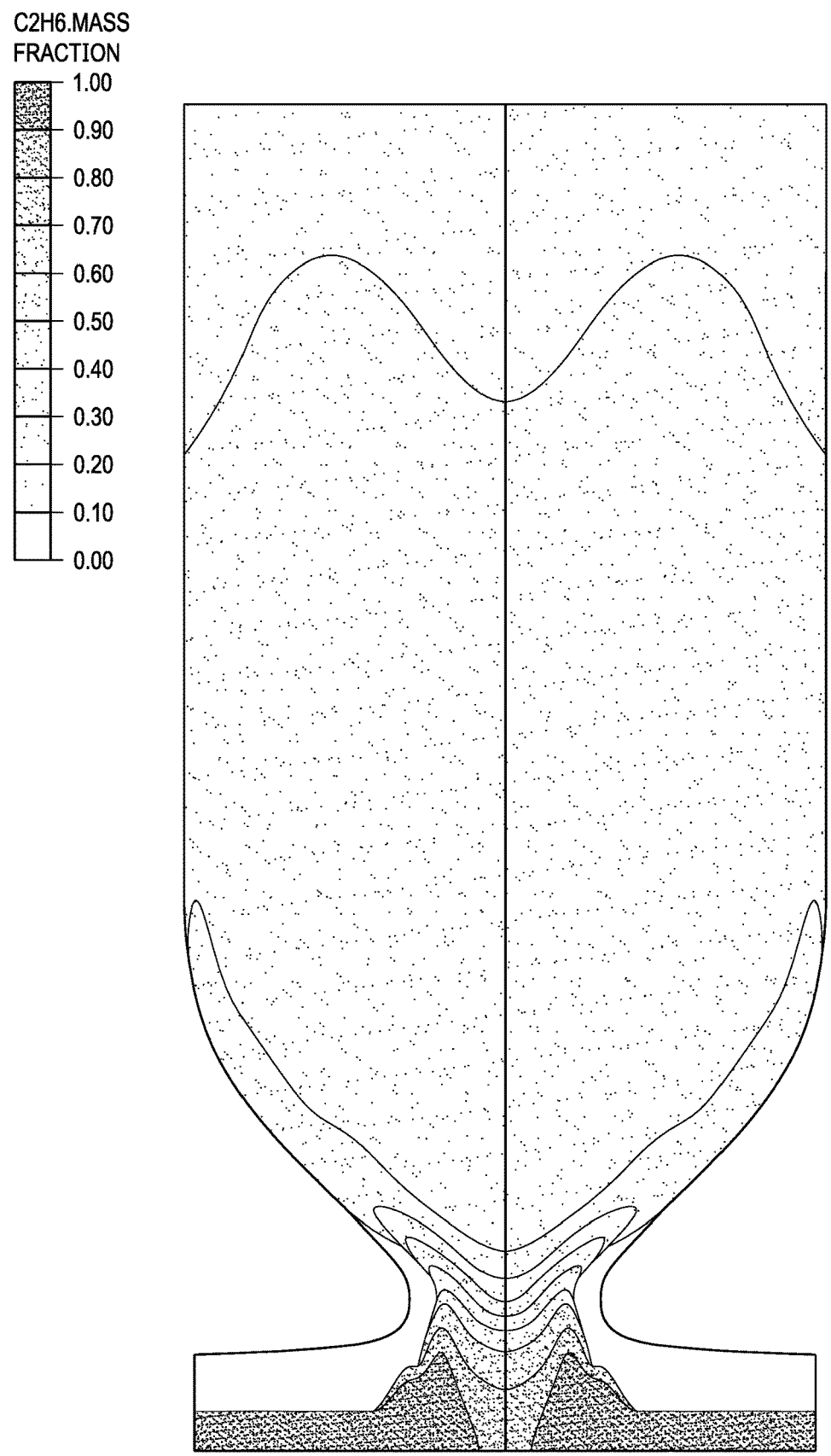
FIG. 15 is a representation of the cracking reactor geometry and mass fraction distribution for ethane cracking feed of the lab scale reactor unit of Example 1.

FIG. 15 shows the mass fraction distribution of the ethane ($C_2H_6$) cracking feed within the reactor system.

Figure 16:
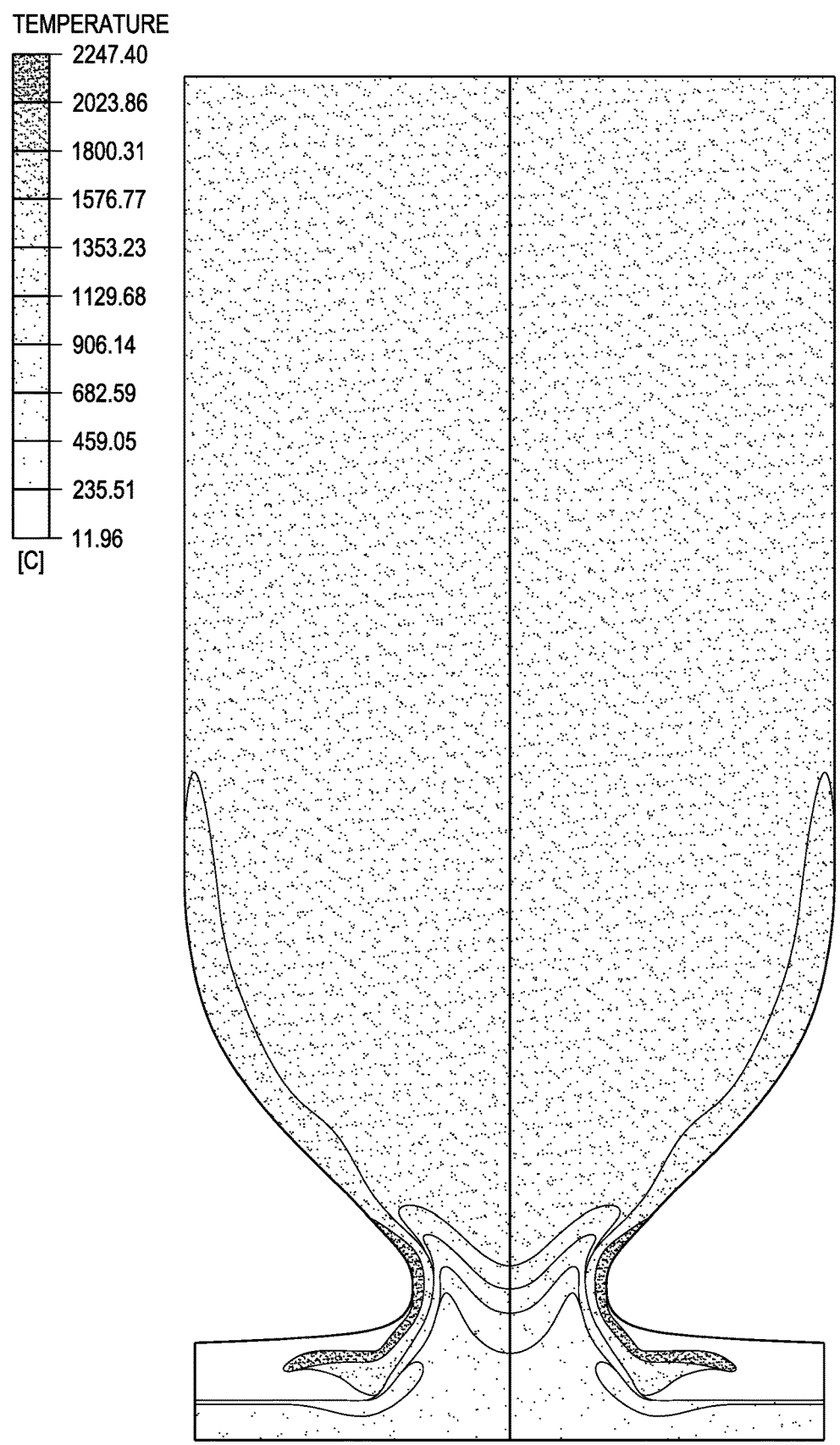
FIG. 16 is a representation of the cracking reactor geometry and the temperature distribution of the lab scale reactor unit of Example 1.

FIG. 16 shows the temperature profile of the reactor system. As shown, the combustion occurs within the combustion zone, corresponding to combustion zone 86 of the feed assembly 58 of FIG. 2, with the higher temperatures from the combustion gases being located along the converging neck portion. Additionally, the steam feed provides a thin cooler layer immediately adjacent to the constricted neck portion. The temperature within the reactor itself is uniformly maintained at approximately 1200° C.

Figure 17:
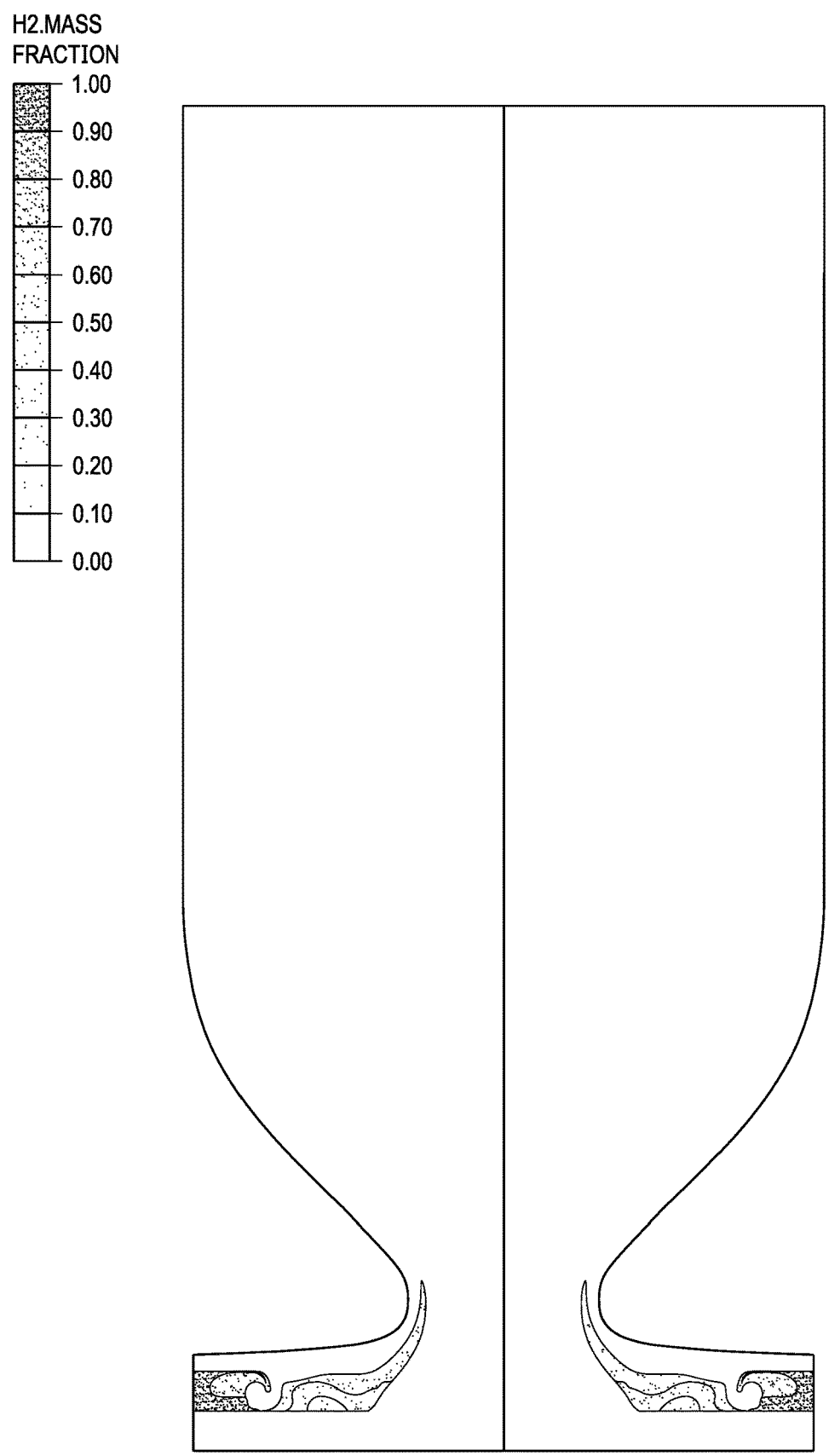
FIG. 17 is a representation of the cracking reactor geometry and mass fraction distribution for hydrogen gas (H$_2$) of the lab scale reactor unit of Example 1.
Figure 18:
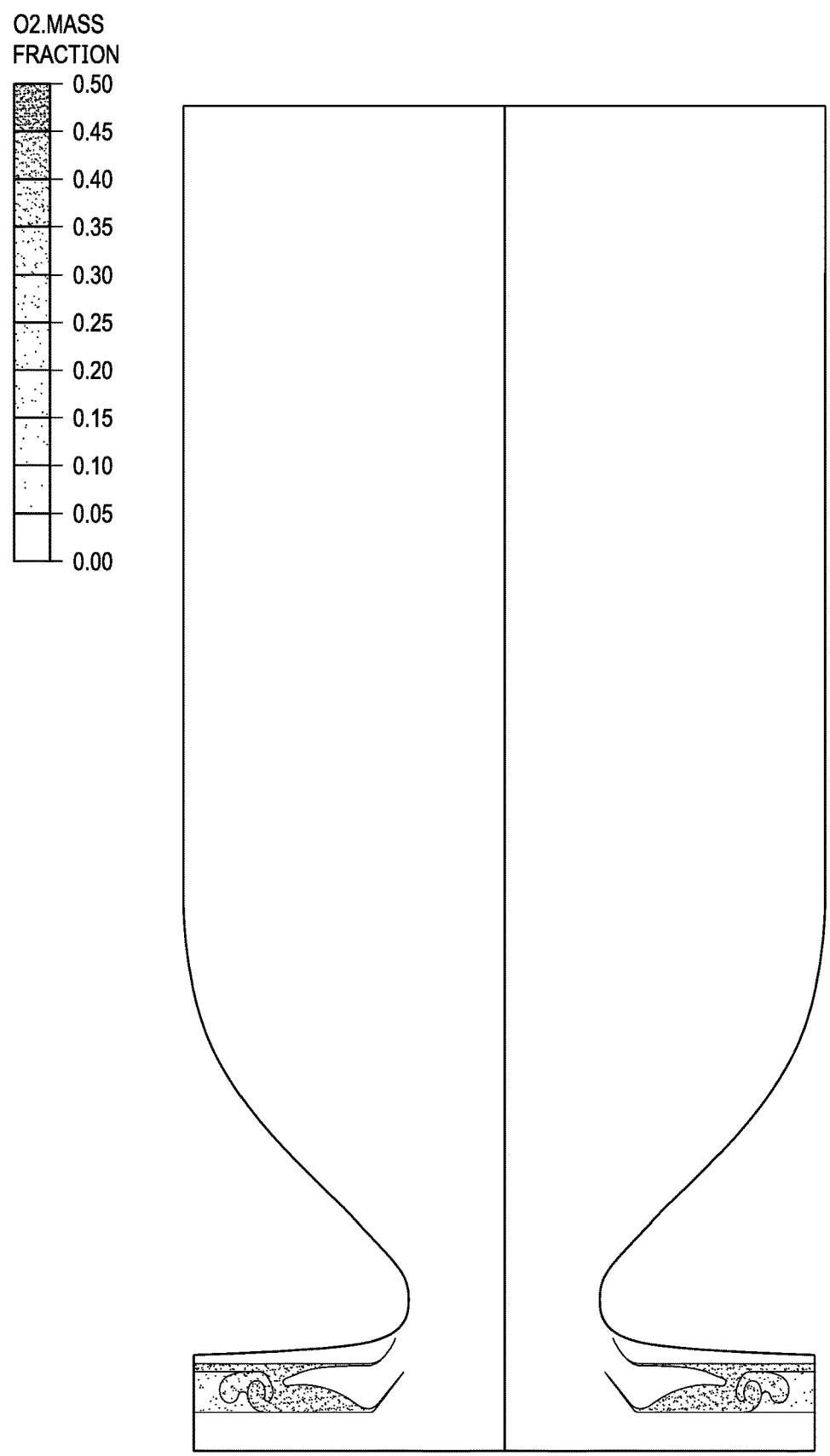
FIG. 18 is a representation of the cracking reactor geometry and mass fraction distribution for oxygen gas (O$_2$) of the lab scale reactor unit of Example 1.
Figure 19:
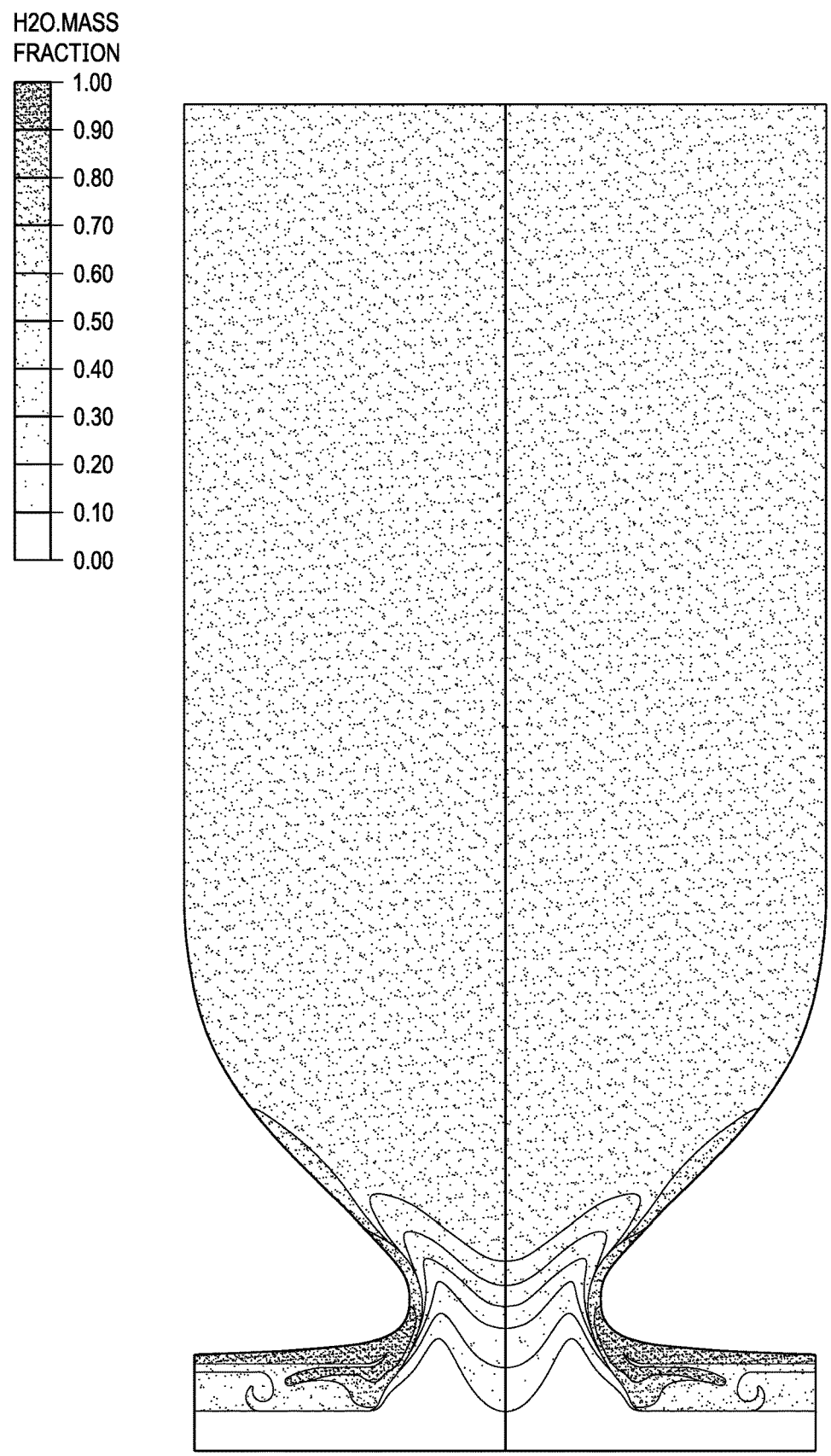
FIG. 19 is a representation of the cracking reactor geometry and mass fraction distribution for steam (H$_2$O) of the lab scale reactor unit of Example 1.

FIGS. 17, 18, and 19 show the mass fraction distribution of the hydrogen gas, oxygen gas, and steam, respectively, within the reactor system. As can be seen in FIG. 17, almost all of the feed hydrogen is burned in the combustion zone. Hydrogen produced by cracking is uniformly distributed in the cylindrical part of the reactor. As can be seen in FIG. 18 all of the oxygen gas is immediately consumed within the combustion zone of the feed assembly, corresponding to combustion zone 86 of the feed assembly 58 of FIG. 2. As can be seen in FIG. 19, all the feed steam introduced through the steam inlet flow space protects the nozzle wall from overheating. All these components are uniformly distributed in the cylindrical part.

Figure 20:
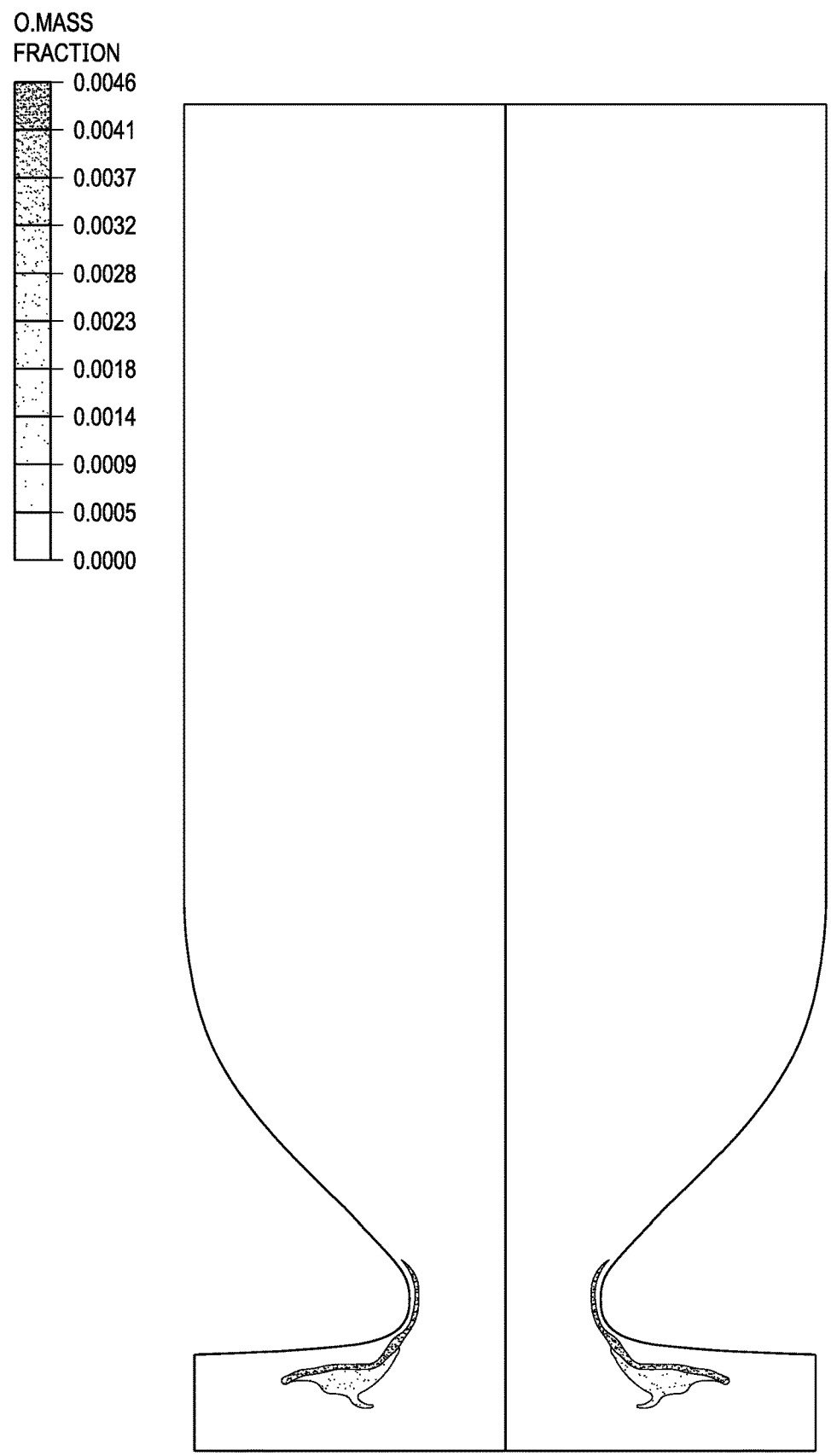
FIG. 20 is a representation of the cracking reactor geometry and mass fraction distribution for atomic oxygen (O) of the lab scale reactor unit of Example 1.

FIG. 20 shows the mass fraction distribution of atomic oxygen (O), which is produced and consumed within the combustion zone and nearly absent with the reactor system.

Figure 21:
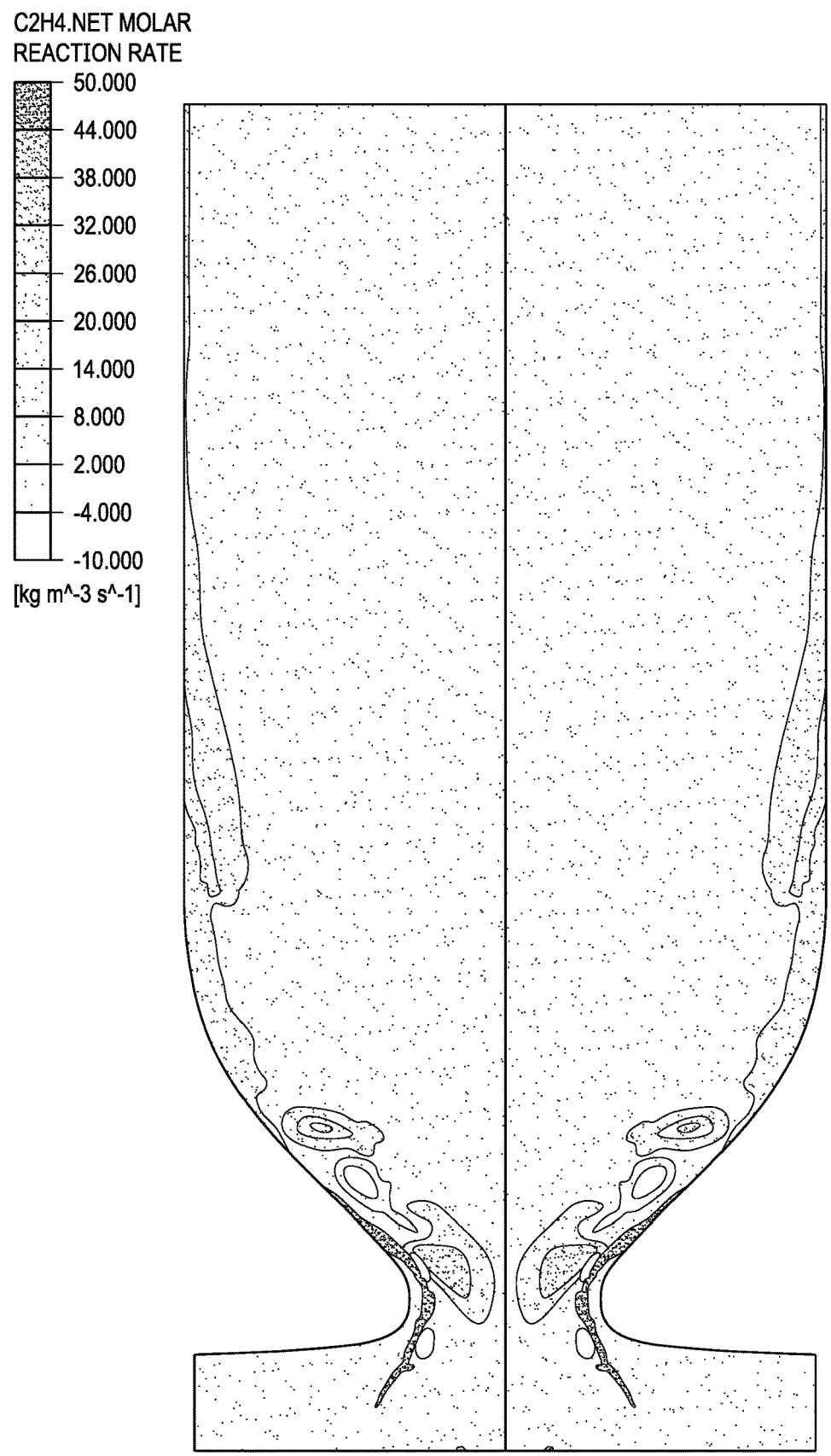
FIG. 21 is a representation of the cracking reactor geometry and mass fraction distribution for the cracked product ethylene of the lab scale reactor unit of Example 1.
Figure 22:
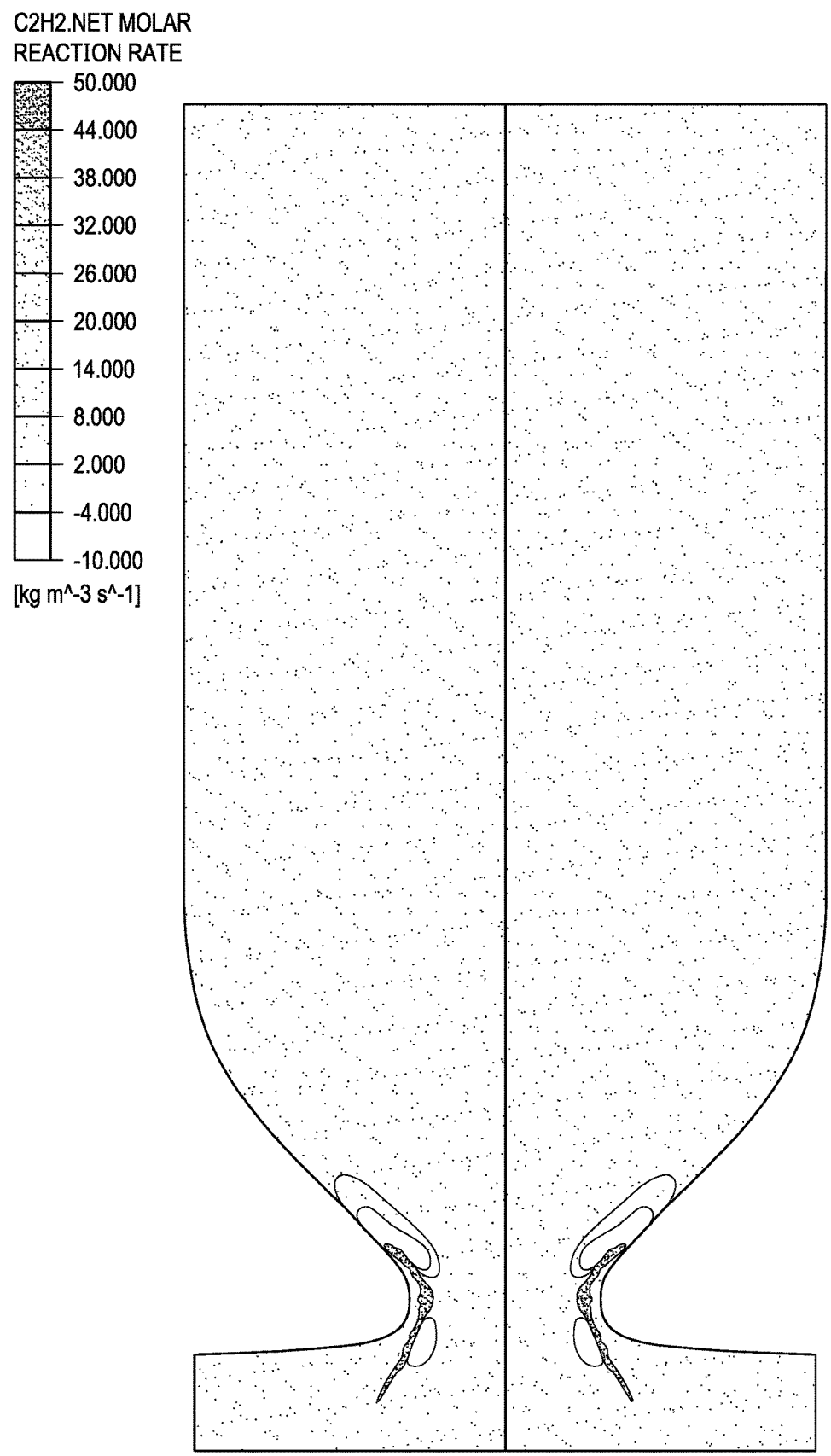
FIG. 22 is a representation of the cracking reactor geometry and mass fraction distribution for the cracked product acetylene of the lab scale reactor unit of Example 1.
Figure 23:
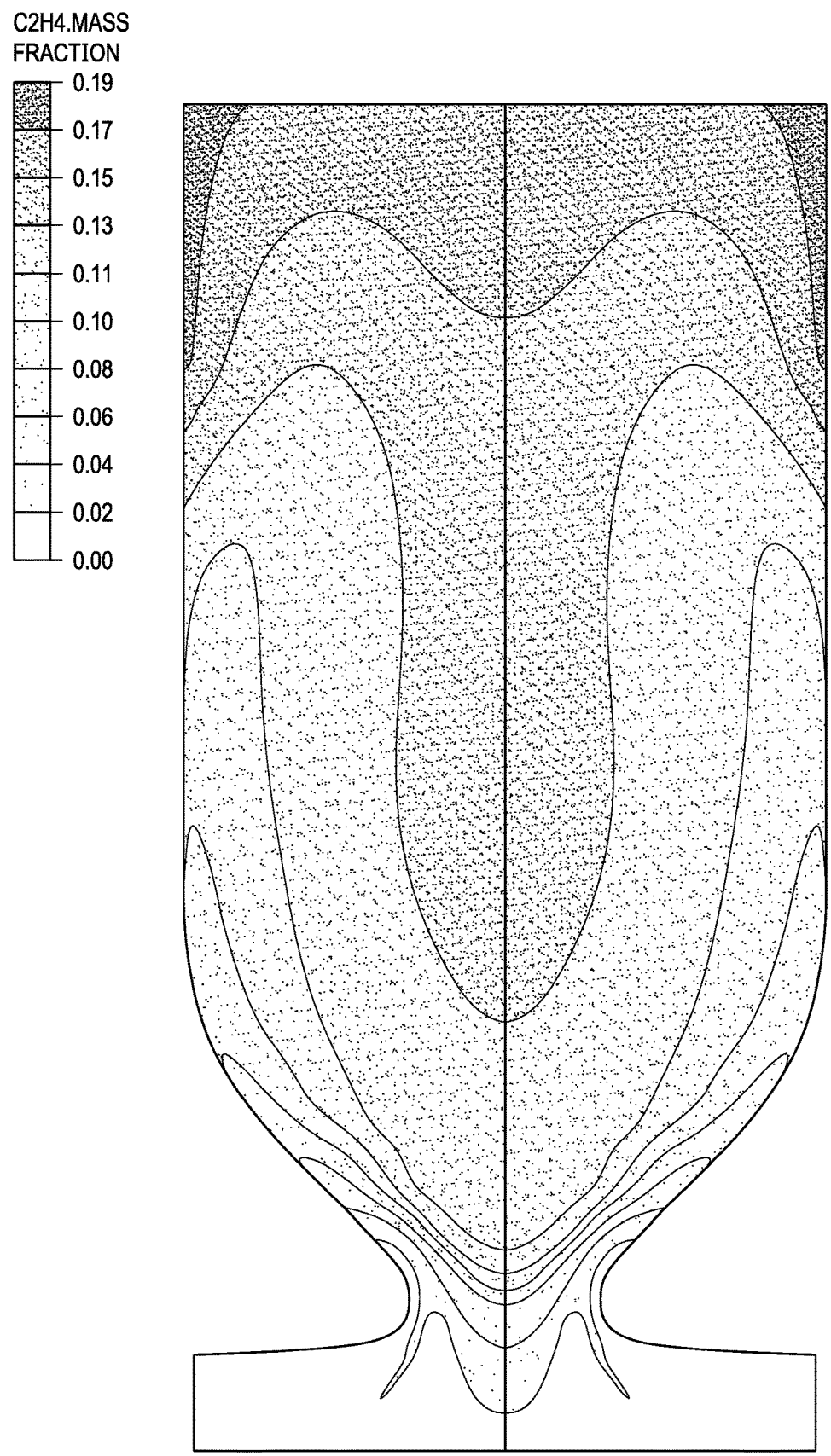
FIG. 23 is a representation of the cracking reactor geometry and mass fraction distribution for the cracked product propylene of the lab scale reactor unit of Example 1.

FIGS. 21, 22, and 23 show the mass fraction distribution of the cracked products of ethylene, acetylene, and propylene, respectively, formed within the reactor system. FIG. 21 shows that $C_2H_4$ is mostly produced in the nozzle and near the reactor wall. FIG. 22 shows that $C_2H_2$ is mostly produced in the nozzle. FIG. 23 shows that the cracking finishes around two diameters axial distance downstream of the nozzle neck.

Figure 24:
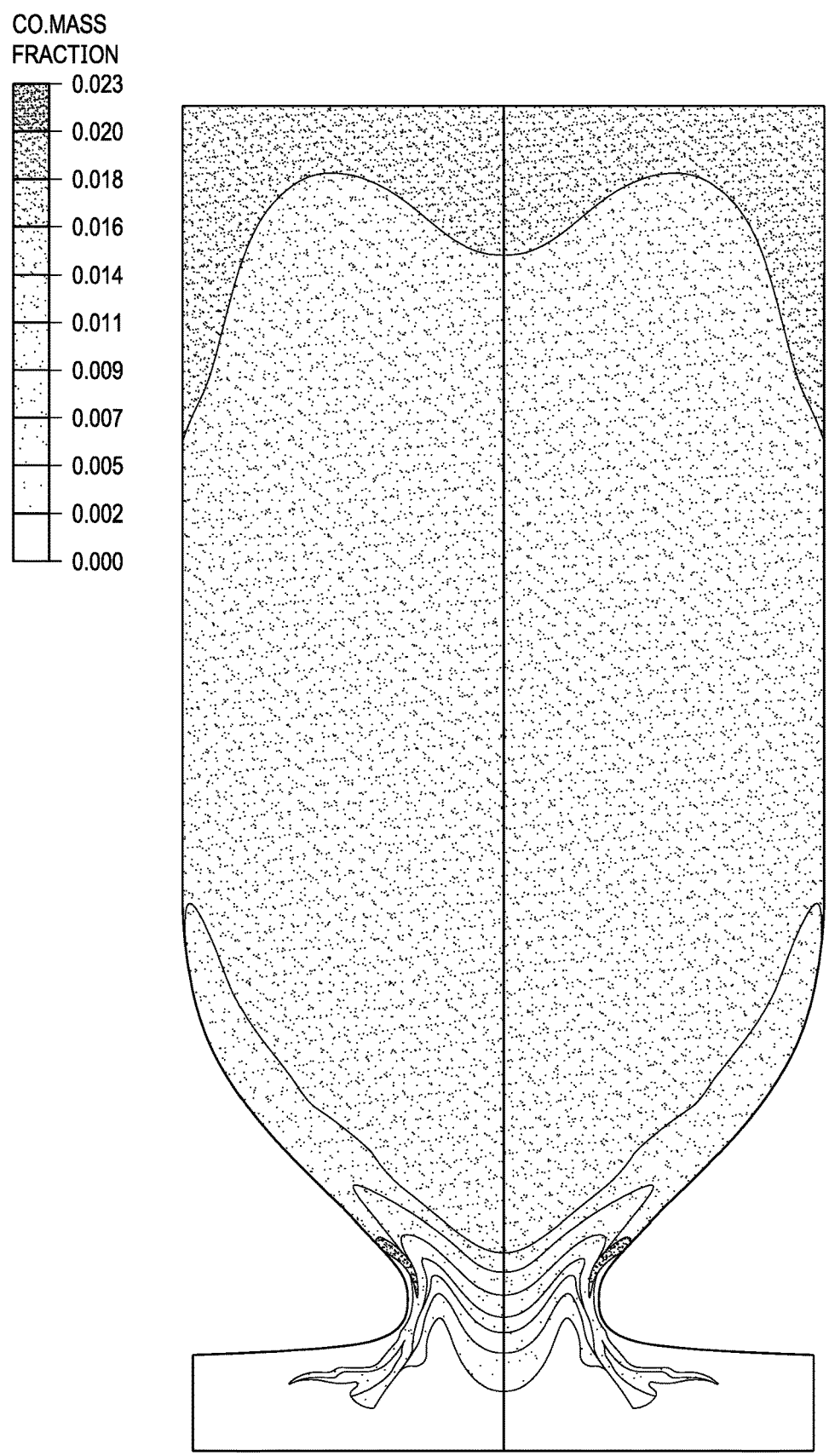
FIG. 24 is a representation of the cracking reactor geometry and mass fraction distribution for carbon monoxide (CO) of the lab scale reactor unit of Example 1

FIG. 24 shows the mass fraction distribution of the CO within the reactor system. The CO is produced near the nozzle neck because only 94% oxygen is burned within the combustion zone. The remaining 6% of oxygen reacts with the hydrocarbons.

Example 2

Along with the CFD simulations, a reactor network model was used with a detailed mechanism in order to examine the chemical kinetics limit and the maximum performance metrics of this novel design on varying feedstock. One simulation (Case 1) was conducted with $H_2$ as fuel and $C_2H_6$ as the cracking hydrocarbon similar to the CFD simulation in EXAMPLE 1. A second simulation (Case 2) was conducted with $H_2$ as fuel and Naphtha (NP) as the cracking hydrocarbon. A third simulation (Case 3) was also conducted using $CH_4$ as the fuel gas for naphtha cracking. The results were compared to a conventional ethane cracker and a conventional naphtha. The results are presented in Table 1 below:

TABLE 1

|  | *Ethane Cracker | Case 1: ANJEVOC-C Fuel $H_2$ = 100% Cracker gas: $C_2H_6$ | *Naphtha Cracker4 | Case 2: ANJEVOC-C Fuel $H_2$ = 100% Cracker gas: NP | Case 3: ANJEVOC-C Fuel $CH_4$ = 100% Cracker gas: NP |
|---|---|---|---|---|---|
| Selectivity $C_2H_4$ & $C_2H_2/C_3H_6$ (%) | 77.6 | 84 (83 from CFD) | 48 | 66 | 77 |
| Conversion of Crack Gas (%) | 65 | 95 (65 from CFD) | 95 | 100 | 100 |
| Total C2/C3 Olefin Yield/ pass (%) | 53 | 80 | 46 | 66 | 77 (42 if $CH_4$ is included) |
| Temperature [° C.] | 840-860 | 1227 | 820~840 | 1243 | 1067 |
| Residence Time [ms] | 100~600 | ~5 | 100~600 | ~4 | ~15 |

The results show that the crack gas conversion and $C_2/C_3$ selectivity of ANJEVOC-C reactor are better than the conventional ethane and naphtha steam cracker due to the direct mixing and heat transfer, favorable operating temperature, and short residence time.

While the invention has been shown in some of its forms, it should be apparent to those skilled in the art that it is not so limited, but is susceptible to various changes and modifications without departing from the scope of the invention based on experimental data or other optimizations considering the overall economics of the process. Accordingly, it is appropriate that the appended claims be construed broadly and in a manner consistent with the scope of the invention.

We claim:

1. A reactor system for the conversion of hydrocarbons comprising:

a reactor vessel having a reactor wall that defines a reaction chamber;

a reactor inlet assembly having a converging conduit with a circumferential wall that surrounds a central longitudinal axis and extends from opposite upstream and downstream ends of the converging conduit, the circumferential wall tapering in width from the downstream and upstream ends to an annular constricted neck portion located between the downstream and upstream ends of the converging conduit, the downstream end of the converging conduit being in fluid communication with the reaction chamber of the reactor, the upstream end of the converging conduit forming an inlet of the reactor inlet assembly;

a feed assembly in fluid communication with the inlet of the reactor inlet assembly, with the central axis passing through the feed assembly, the feed assembly comprising:

a downstream feed assembly wall (60) that extends circumferentially around and joins the upstream end of the reactor inlet assembly, the downstream feed assembly wall being oriented perpendicular or substantially perpendicular to the central axis;

an upstream feed assembly wall (62) that is axially spaced upstream from the downstream feed assembly wall (60) along the central axis and extends perpendicularly or substantially perpendicular across the central axis;

an upstream gas partition wall (64) and a downstream gas partition wall (66) that are each axially spaced between the downstream and upstream feed assembly walls and are axially spaced from one another, the upstream gas partition wall and the downstream gas partition wall or circumferential portions thereof being oriented perpendicular or substantially perpendicular to the central axis, at least one of the upstream gas partition wall (64) and the downstream gas partition wall (66) terminates at a position upstream from the converging conduit to define a central opening (68, 70) that surrounds the central axis of the converging conduit, an upstream annular inlet flow space (72) being defined between the upstream feed assembly wall (62) and the upstream partition wall (64), an annular downstream inlet flow space (74) being defined between the downstream feed assembly wall (60) and the downstream gas partition wall (66), and an intermediate inlet flow space (76) defined between the upstream gas partition wall (64) and the downstream gas partition wall (66); wherein;

said annular inlet flow spaces cause introduced feeds to flow perpendicularly or substantially perpendicular toward the central axis of the converging conduit in an inwardly swirling fluid flow pattern within said flow spaces about the central axis of the converging conduit; and wherein the area extending from the central opening of the at least one of the upstream and downstream partition walls to the inlet of the reactor inlet assembly defines a central chamber of the feed assembly, with hot combustion gases from at least one of the inlet flow spaces being discharged into the central chamber, with the hydrocarbon feed and heated combustion gases passing as swirling gases through the converging conduit to the reaction chamber.

2. The reactor system of claim 1, wherein:
at least one of the annular inlet flow spaces is provided with circumferentially spaced apart guide vanes oriented to facilitate the swirling fluid flow within said at least one of the inlet flow spaces.

3. The reactor system of claim 2, wherein:
the guide vanes are movable to selected positions and tilting angles to provide selected azimuthal-to-radial velocity ratios of fluids flowing within the annular inlet flow spaces.

4. The reactor system of claim 2, wherein:
the guide vanes are configured as non-planar airfoils.

5. The reactor system of claim 1, wherein:
the reactor wall is cylindrical.

6. The reactor system of claim 1, wherein:
the circumferential wall of the converging conduit from the downstream end to the annular constricted neck portion, and optionally an upstream portion of the reactor wall of the reaction chamber that joins the circumferential wall of the converging conduit, is configured as a smooth, continuous wall that follows contour lines of an ellipsoidal cap or spherical cap shape.

7. The reactor system of claim 1, wherein:
the downstream gas partition wall has an extended portion that is spaced from and follows the contours of the circumferential wall of the converging conduit of the reactor inlet assembly and terminates at a position downstream of the annular constricted neck portion so that a downstream inlet flow space is defined that discharges into an area downstream from the constricted neck portion.

8. The reactor system of claim 1, wherein:
at least one of A and B, wherein:
A is the intermediate annular gas inlet flow space is divided by an intermediate gas partition wall having a central opening that surrounds the central axis of the converging conduit and divides the intermediate inlet flow space into upstream and downstream intermediate annular inlet flow spaces that constitute\inlet flow spaces for introducing a fuel gas feed and an oxidizer feed; and
B is the upstream annular gas inlet flow space and the intermediate inlet flow space constitute inlet flow spaces for introducing a fuel gas feed and an oxidizer feed.

9. The reactor system of claim 1, further comprising:
a cooling gas feed assembly in fluid communication with at least one of the reaction chamber and the reactor inlet assembly, the cooling gas feed assembly comprising:
a pair of axially spaced apart cooling gas feed assembly walls oriented perpendicular or substantially perpendicular to the central axis, an annular cooling gas inlet flow space being defined between the cooling gas feed assembly walls and communicates with said at least one of the reaction chamber and the reactor inlet assembly.

10. The reactor system of claim 9, wherein:
the annular cooling gas inlet flow space is provided with circumferentially spaced apart guide vanes oriented to facilitate the swirling fluid flow within said cooling gas inlet flow space.

11. A method of cracking hydrocarbons to cracked hydrocarbon products, the method comprising:
introducing a hydrocarbon feed containing hydrocarbons to be cracked into a reactor system comprising:
a reactor vessel having a reactor wall that defines a reaction chamber;

a reactor inlet assembly having a converging conduit with a circumferential wall that surrounds a central longitudinal axis and extends from opposite upstream and downstream ends of the converging conduit, the circumferential wall tapering in width from the downstream and upstream ends to an annular constricted neck portion located between the downstream and upstream ends of the converging conduit, the downstream end of the converging conduit being in fluid communication with the reaction chamber of the reactor, the upstream end of the converging conduit forming an inlet of the reactor inlet assembly;

a feed assembly in fluid communication with the inlet of the reactor inlet assembly, with the central axis passing through the feed assembly, the feed assembly comprising:

a downstream feed assembly wall that extends circumferentially around and joins the upstream end of the reactor inlet assembly, the downstream feed assembly wall being oriented perpendicular or substantially perpendicular to the central axis;

an upstream feed assembly wall that is axially spaced upstream from the downstream feed assembly wall along the central axis and extends perpendicularly or substantially perpendicularly across the central axis;

an upstream gas partition wall and a downstream gas partition wall that are each axially spaced between the downstream and upstream feed assembly walls and are axially spaced from one another, the upstream gas partition wall and the downstream gas partition wall or circumferential portions thereof being oriented perpendicular or substantially perpendicular to the central axis, at least one of the upstream gas partition wall (64) and downstream gas partition wall terminates at a position upstream from the converging conduit to define a central opening that surrounds the central axis of the converging conduit, an upstream annular inlet flow space being defined between the upstream feed assembly wall and the upstream partition wall, a downstream annular inlet flow space being defined between the downstream feed assembly wall and the downstream gas partition wall, and an intermediate inlet flow space defined between the upstream gas partition wall and the downstream gas partition wall; wherein;

said annular inlet flow spaces causes introduced feeds to flow perpendicularly or substantially perpendicularly toward the central axis of the converging conduit in an inwardly swirling fluid flow pattern within said flow spaces about the central axis of the converging conduit; and wherein the area extending from the central opening of the at least one upstream and downstream partition walls to the inlet of the reactor inlet assembly defines a central chamber of the feed assembly; and wherein a cracking feed of the hydrocarbon feed to be cracked is introduced into a first inlet flow space and a fuel gas feed and an oxidizer feed is introduced into adjacent second and third inlet flow spaces so that the feeds pass through said flow spaces perpendicularly or substantially perpendicularly toward the central axis of the converging conduit in an inwardly swirling fluid flow pattern within said flow spaces flowing about the central axis of the converging conduit, the fuel gas feed and oxidizer feed combusting in the central chamber to form hot combustion gases, the hot combustion gases and cracking feed being discharged into the central chamber and/or reaction chamber so that the hot combustion gases and cracking feed are mixed together and form a swirling, heated gas mixture;

allowing the heated gas mixture to react within the reaction chamber of the reactor vessel under reaction conditions suitable for hydrocarbon cracking, with at least a portion of the cracking feed of the gas mixture being converted to cracked hydrocarbon products; and removing a cracked hydrocarbon product from the reaction chamber of the reactor vessel.

12. The method of claim 11, wherein:

the oxidizer feed comprises an oxygen-containing gas ($O_2$) and the fuel gas feed comprises hydrogen-containing gas of at least one of hydrogen gas ($H_2$) and methane ($CH_4$), the oxygen-containing gas being introduced into one of the first and second annular fuel gas inlet flow spaces and the hydrogen-containing gas being introduced into the other.

13. The method of claim 12, wherein:

the hydrogen-containing gas is introduced into the feed assembly to provide an excess of hydrogen that is from 1 to 5 times that required for combustion of the fuel gas feed.

14. The method of claim 11, wherein:

the cracking feed comprises at least one of ethane, liquefied petroleum gas, butane, naphtha, natural gas, light gas oils, and heavy gas oils, the cracking feed optionally being premixed with steam.

15. The method of claim 11, wherein:

at least one of hydrogen gas ($H_2$), methane, and carbon oxides are separated from the removed cracked hydrocarbon product and recycled to the feed assembly.

16. The method of claim 11, wherein:

the azimuthal-to-radial velocity ratio of each of the feeds and the oxygen gas feed stream within the annular flow spaces is from 0 to $\infty$.

17. The method of claim 11, wherein:

at least one of the annular inlet flow spaces is provided with circumferentially spaced apart guide vanes oriented to facilitate the spiraling fluid flow within said at least one of the inlet flow spaces.

18. The method of claim 11, wherein:

the reactor system further comprises a cooling gas feed assembly in fluid communication with at least one of the reaction chamber and the reactor inlet assembly, the cooling gas feed assembly comprising a pair of axially spaced apart cooling gas feed assembly walls oriented perpendicular or substantially perpendicular to the central axis, an annular cooling gas inlet flow space being defined between the cooling gas feed assembly walls that communicates with said at least one of the reaction chamber and the reactor inlet assembly where cooling gases from the cooling gas feed assembly are introduced.

19. The method of claim 11, wherein:

the residence time of the gas mixture within the reactor system is 50 milliseconds or less.

20. The method of claim 11, wherein:

the reaction conditions include at least one of temperature of from 900° C. to 1300° C. and a pressure of from 0 kPa (g) to 10,000 kPa (g) at an outlet of the reactor.

* * * * *